(12) United States Patent
Addison et al.

(10) Patent No.: US 11,367,525 B2
(45) Date of Patent: Jun. 21, 2022

(54) CALIBRATION FOR CONTINUOUS NON-INVASIVE BLOOD PRESSURE MONITORING USING ARTIFICIAL INTELLIGENCE

(71) Applicant: Covidien LP, Mansfield, MA (US)

(72) Inventors: Paul S. Addison, Edinburgh (GB); Dean Montgomery, Edinburgh (GB); Andre Antunes, Edinburgh (GB)

(73) Assignee: COVIDIEN LP, Mansfield, MA (US)

(*) Notice: Subject to any disclaimer, the term of this patent is extended or adjusted under 35 U.S.C. 154(b) by 408 days.

(21) Appl. No.: 16/723,678

(22) Filed: Dec. 20, 2019

(65) Prior Publication Data
US 2021/0193311 A1    Jun. 24, 2021

(51) Int. Cl.
| A61B 5/1455 | (2006.01) |
| A61B 5/024 | (2006.01) |
| A61B 5/0205 | (2006.01) |
| G16H 40/40 | (2018.01) |
| A61B 5/00 | (2006.01) |
| A61B 5/021 | (2006.01) |
| A61B 5/08 | (2006.01) |

(52) U.S. Cl.
CPC ........... *G16H 40/40* (2018.01); *A61B 5/0205* (2013.01); *A61B 5/02108* (2013.01); *A61B 5/02416* (2013.01); *A61B 5/14551* (2013.01); *A61B 5/7267* (2013.01); *A61B 5/0806* (2013.01); *A61B 5/7278* (2013.01); *A61B 2560/0238* (2013.01)

(58) Field of Classification Search
CPC ... A61B 5/1455; A61B 5/7267; A61B 5/0205; A61B 5/02416; A61B 5/0806; A61B 5/7278
See application file for complete search history.

(56) References Cited

U.S. PATENT DOCUMENTS

| 9,301,697 B2 | 4/2016 | Baker, Jr. et al. |
| 9,861,317 B2 | 1/2018 | Ochs |

(Continued)

FOREIGN PATENT DOCUMENTS

EP    3430991 A1    1/2019

OTHER PUBLICATIONS

International Search Report and Written Opinion from International Application No. PCT/US2020/066000, dated Apr. 12, 2021, 16 pp.

(Continued)

*Primary Examiner* — Eric F Winakur
(74) *Attorney, Agent, or Firm* — Shumaker & Sieffert, P.A.

(57) ABSTRACT

A system for continuous non-invasive blood pressure monitoring may include processing circuitry configured to determine calibration data for a continuous non-invasive blood pressure model at a calibration point, receive, from an oxygen saturation sensing device, a PPG signal at a particular time subsequent to the calibration point, derive values of the set of metrics for the patient from the PPG signal, and determine, using the continuous non-invasive blood pressure model and based at least in part on inputting the calibration data determined at the calibration point, the values of the set of metrics, and an elapsed time at the particular time since the calibration point into the continuous non-invasive blood pressure model, a blood pressure of the patient at the particular time.

20 Claims, 8 Drawing Sheets

(56) References Cited

U.S. PATENT DOCUMENTS

2012/0136605 A1* 5/2012 Addison ............ A61B 5/02125
702/98
2013/0012823 A1 1/2013 Ripoll et al.
2016/0198963 A1 7/2016 Addison et al.
2017/0258340 A1* 9/2017 Przybyszewski .. A61B 5/02125
2018/0303434 A1* 10/2018 Selvaraj ............... A61B 5/0205

OTHER PUBLICATIONS

Meng et al., "A Multi-feature Fusion Method to Estimate Blood Pressure by PPG," Springer International Publishing AG, DOI:10.1007/978-3-319-59858-1_12, 2017 (Applicant points out, in accordance with MPEP 609.04(a), that the year of publication, 2017, is sufficiently earlier than the effective U.S. filing date, so that the particular month of publication is not in issue ), pp. 121-131.
Khalid et al., "Blood Pressure Estimation Using Photoplethysmography Only: Comparison between Different Machine Learning Approaches," Hindawi Journal of Healthcare Engineering: vol. 2018, Oct. 23, 2018, 13 pp.
Tabatabai, "Cuff-less and calibration free blood pressure estimation using the pulse transit time method," Learning from Data Project; ECE 699-002, 2015, 5 pp. (Applicant points out, in accordance with MPEP 609.04(a), that the year of publication, 2015, is sufficiently earlier than the effective U.S. filing date, so that the particular month of publication is not in issue.

* cited by examiner

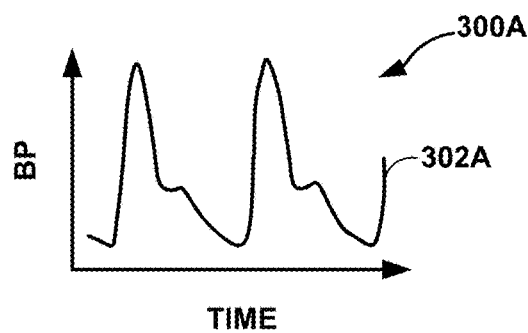
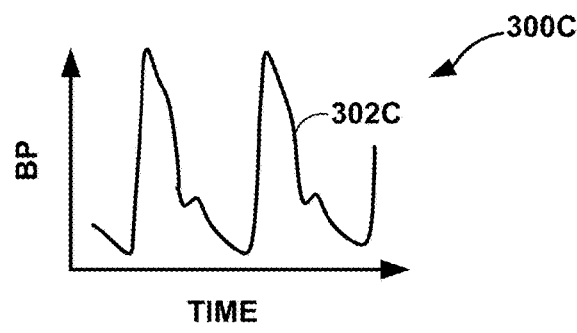
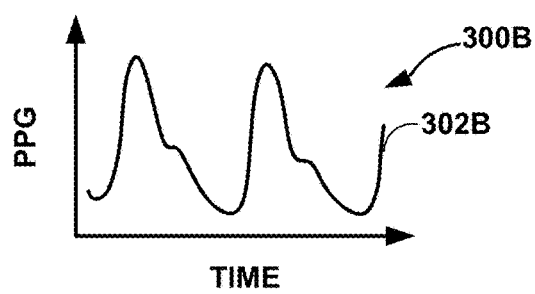
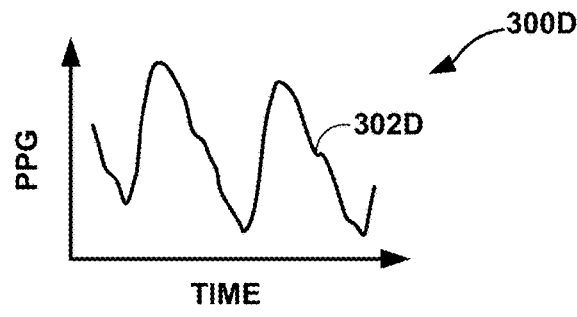
FIG. 3A
FIG. 3B
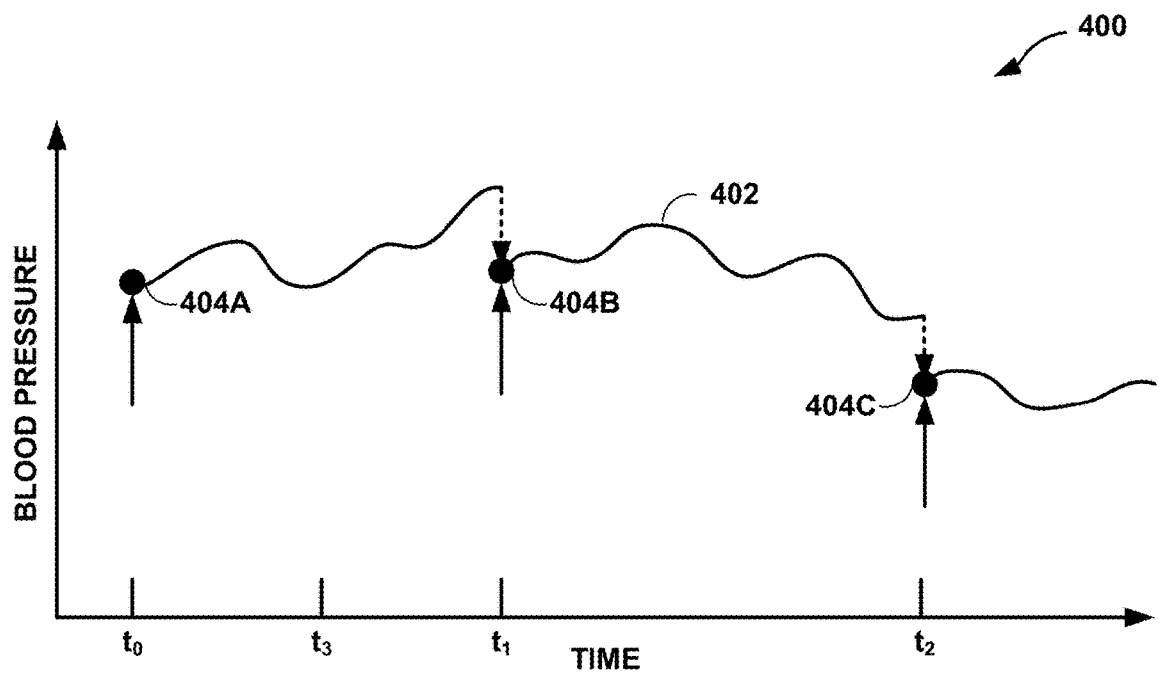
FIG. 4

```
┌─────────────────────────────────────────────────────┐
│ DETERMINING CALIBRATION DATA FOR A CONTINUOUS NON-  │
│ INVASIVE BLOOD PRESSURE MODEL AT A CALIBRATION POINT BY: │
│ RECEIVING A BLOOD PRESSURE MEASUREMENT OF A PATIENT │
│ FROM A BLOOD PRESSURE SENSING DEVICE AT THE CALIBRATION │──── 902
│ POINT, RECEIVING A FIRST PHOTOPLETHYSMOGRAPHIC (PPG)│
│ SIGNAL FROM AN OXYGEN SATURATION SENSING DEVICE AT THE │
│ CALIBRATION POINT, AND DERIVING FIRST VALUES OF A SET OF │
│ METRICS FOR THE PATIENT FROM THE FIRST PPG SIGNAL.  │
└─────────────────────────────────────────────────────┘
                            │
                            ▼
┌─────────────────────────────────────────────────────┐
│ RECEIVING A SECOND PPG SIGNAL FROM THE OXYGEN       │
│ SATURATION SENSING DEVICE AT A PARTICULAR TIME      │──── 904
│ SUBSEQUENT TO THE CALIBRATION POINT.                │
└─────────────────────────────────────────────────────┘
                            │
                            ▼
┌─────────────────────────────────────────────────────┐
│ DERIVING SECOND VALUES OF THE SET OF METRICS FOR THE│──── 906
│ PATIENT FROM THE SECOND PPG SIGNAL.                 │
└─────────────────────────────────────────────────────┘
                            │
                            ▼
┌─────────────────────────────────────────────────────┐
│ DETERMINING, USING THE CONTINUOUS NON-INVASIVE BLOOD│
│ PRESSURE MODEL AND BASED AT LEAST IN PART ON INPUTTING │
│ THE CALIBRATION DATA DETERMINED AT THE CALIBRATION  │
│ POINT, THE SECOND VALUES OF THE SET OF METRICS, AND AN │──── 908
│ ELAPSED TIME AT THE PARTICULAR TIME SINCE THE       │
│ CALIBRATION POINT INTO THE CONTINUOUS NON-INVASIVE  │
│ BLOOD PRESSURE MODEL, A BLOOD PRESSURE OF THE PATIENT │
│ AT THE PARTICULAR TIME.                             │
└─────────────────────────────────────────────────────┘
```

FIG. 9

CALIBRATION FOR CONTINUOUS NON-INVASIVE BLOOD PRESSURE MONITORING USING ARTIFICIAL INTELLIGENCE

BACKGROUND

Continuous non-invasive blood pressure (CNIBP) monitoring systems allow a blood pressure of a patient to be tracked continuously, unlike standard occlusion cuff techniques. In some examples, pulse oximetry sensors may be placed on a patient to measure photoplethysmograph (PPG) signals, and such PPG signals may be used to estimate the blood pressure of the patient. The CNIBP monitoring system may periodically recalibrate the CNIBP monitoring system based on blood pressure measured by a non-invasive blood pressure monitoring system, such as an inflatable cuff-type blood pressure monitoring system.

SUMMARY

The present disclosure describes example devices, systems, and techniques for continuous non-invasive blood pressure monitoring of patients via the use of PPG signals in a way that can improve the accuracy of such continuous non-invasive blood pressure monitoring. Rather than solely using PPG signals to determine the blood pressures of patients, the present disclosure describes example techniques for determining calibration data when the continuous non-invasive blood pressure monitoring system is periodically recalibrated and using the most recently determined calibration data along with the PPG signals to determine (e.g., derive) the blood pressures of patients. Further, in some aspects, the present disclosure describes a continuous non-invasive blood pressure model that is trained via machine learning with such determined calibration data so that the model may be able to receive the most recently determined calibration data along with the PPG signals to more accurately determine the blood pressures of patients.

By determining calibration data when the continuous non-invasive blood pressure monitoring system is periodically recalibrated and by using such calibration data to both train a continuous non-invasive blood pressure model and as input into the continuous non-invasive blood pressure model, the devices, systems, and techniques of this disclosure may increase the accuracy of continuous non-invasive blood pressure monitoring algorithms and may enable a continuous non-invasive blood monitoring device to present more accurate information regarding a patient's blood pressure. The presentation of more accurate information may result in more informed decision making by the clinician, compared to continuous non-invasive monitoring systems that do not use such calibration data.

In some examples, a method includes determining calibration data for a continuous non-invasive blood pressure model at a calibration wherein the calibration data comprises: receiving a blood pressure measurement of a patient from a blood pressure sensing device at the calibration point, receiving a first photoplethysmographic (PPG) signal from an oxygen saturation sensing device at the calibration point, and deriving first values of a set of metrics for the patient from the first PPG signal. The method further includes receiving a second PPG signal from the oxygen saturation sensing device at a particular time subsequent to the calibration point. The method further includes deriving second values of the set of metrics for the patient from the second PPG signal. The method further includes determining, using the continuous non-invasive blood pressure model and based at least in part on inputting the calibration data determined at the calibration point, the second values of the set of metrics, and an elapsed time at the particular time since the calibration point into the continuous non-invasive blood pressure model, a blood pressure of the patient at the particular time.

In some examples, a system includes a blood pressure sensing device, an oxygen saturation sensing device, and a processing circuitry configured to: determine calibration data for a continuous non-invasive blood pressure model at a calibration point by at least: receiving, from the blood pressure sensing device, blood pressure measurements of a patient at the calibration point, receiving, from the oxygen saturation sensing device, a first photoplethysmographic (PPG) signal at the calibration point, and deriving first values of a set of metrics for the patient from the first PPG signal; receive, from the oxygen saturation sensing device, a second PPG signal at a particular time subsequent to the calibration point; derive second values of the set of metrics for the patient from the second PPG signal; and determine, using the continuous non-invasive blood pressure model and based at least in part on inputting the calibration data determined at the calibration point, the second values of the set of metrics, and an elapsed time at the particular time since the calibration point into the continuous non-invasive blood pressure model, a blood pressure of the patient at the particular time.

In some examples, a non-transitory computer readable storable medium comprising instructions that, when executed, cause processing circuitry to: determine calibration data for a continuous non-invasive blood pressure model at a calibration point by at least: receiving blood pressure measurements of a patient at the calibration point, receiving a first photoplethysmographic (PPG) signal at the calibration point, and deriving first values of a set of metrics for the patient from the first PPG signal; receive a second PPG signal at a particular time subsequent to the calibration point; derive second values of the set of metrics for the patient from the second PPG signal; and determine, using the continuous non-invasive blood pressure model and based at least in part on inputting the calibration data determined at the calibration point, the second values of the set of metrics, and an elapsed time at the particular time since the calibration point into the continuous non-invasive blood pressure model, a blood pressure of the patient at the particular time.

The details of one or more examples are set forth in the accompanying drawings and the description below. Other features, objects, and advantages will be apparent from the description and drawings, and from the claims.

BRIEF DESCRIPTION OF THE DRAWINGS

FIGS. 3A and 3B illustrate an example divergence of blood pressure measurements and PPG signals.

FIG. 4 illustrates example graph of blood pressure over time as determined using a CNIBP monitoring algorithm that is periodically calibrated with the blood pressure as measured by a non-invasive blood pressure monitoring system.

FIG. 9 is a flow diagram illustrating an example method of determining the blood pressure of a patient using the CNIBP model 124 of FIGS. 1 and 2.

DETAILED DESCRIPTION

Figure 1:
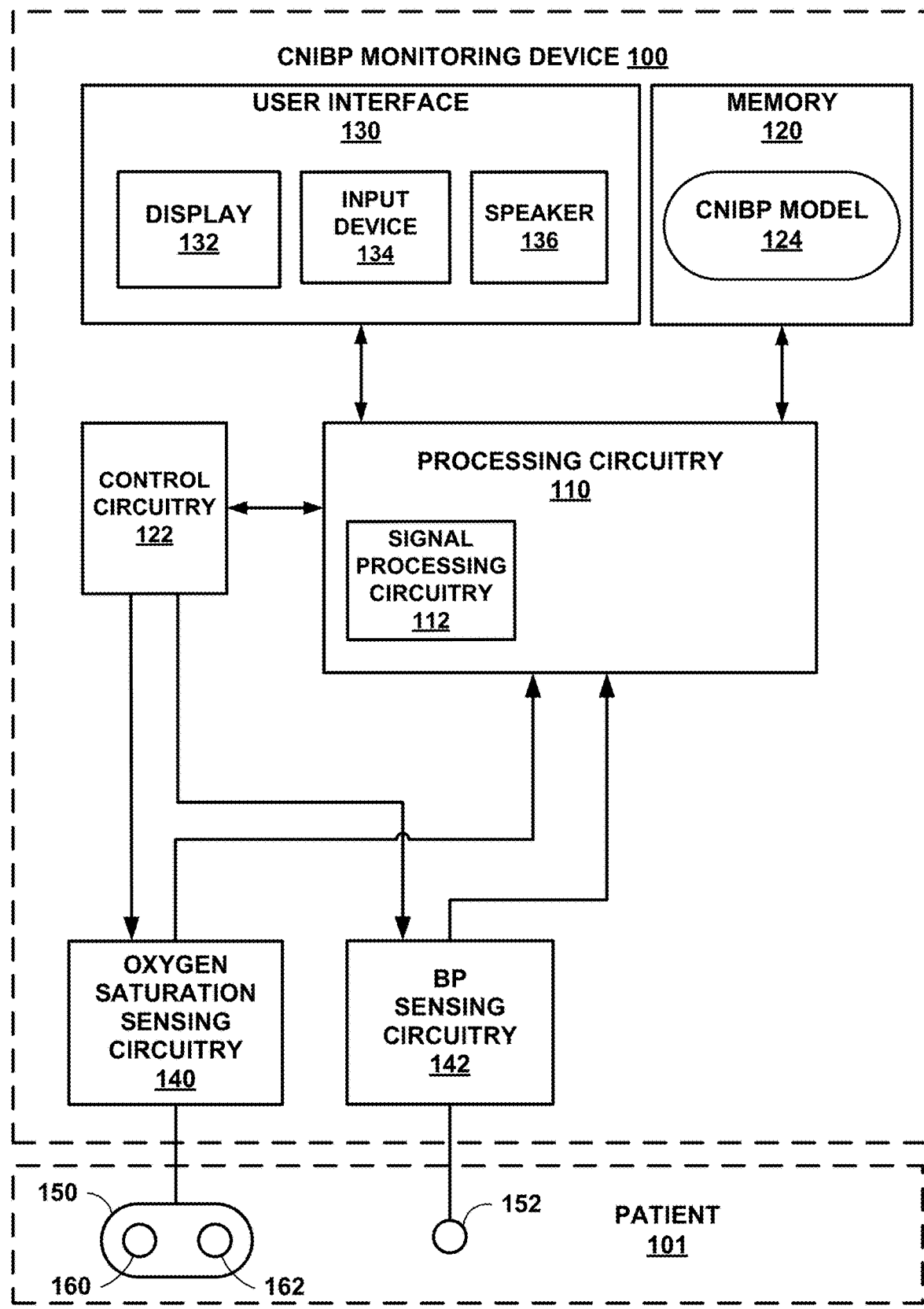
FIG. 1 is a conceptual block diagram illustrating an example continuous non-invasive blood pressure (CNIBP) monitoring device.

FIG. 1 is a conceptual block diagram illustrating an example continuous non-invasive blood pressure monitoring device 100. Continuous non-invasive blood pressure (CNIBP) monitoring device 100 includes processing circuitry 110, memory 120, control circuitry 122, user interface 130, sensing circuitry 140 and 142, and sensing devices 150 and 152. In the example shown in FIG. 1, user interface 130 may include display 132, input device 134, and/or speaker 136, which may be any suitable audio device configured to generate and output a noise. In some examples, CNIBP monitoring device 100 may be configured to determine and output (e.g., for display at display 132) the continuous blood pressure of a patient 101, e.g., during a medical procedure or for more long-term monitoring, such as intensive care unit (ICU) and general post-operation monitoring. A clinician may receive information regarding the continuous non-invasive blood pressure of a patient via user interface 130 and adjust treatment or therapy to patient 101 based on the continuous non-invasive blood pressure information.

Processing circuitry 110, as well as other processors, processing circuitry, controllers, control circuitry, and the like, described herein, may include one or more processors. Processing circuitry 110 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 110 may include multiple components, such as any combination of one or more microprocessors, one or more DSPs, one or more ASICs, or one or more FPGAs, as well as other discrete or integrated logic circuitry, and/or analog circuitry.

Control circuitry 122 may be operatively coupled processing circuitry 110. Control circuitry 122 is configured to control an operation of sensing devices 150 and 152. In some examples, control circuitry 122 may be configured to provide timing control signals to coordinate operation of sensing devices 150 and 152. For example, sensing circuitry 140 and 142 may receive from control circuitry 122 one or more timing control signals, which may be used by sensing circuitry 140 and 142 to turn on and off respective sensing devices 150 and 152, such as to periodically collect calibration data using sensing devices 150 and 152. In some examples, processing circuitry 110 may use the timing control signals to operate synchronously with sensing circuitry 140 and 142. For example, processing circuitry 110 may synchronize the operation of an analog-to-digital converter and a demultiplexer with sensing circuitry 140 and 142 based on the timing control signals.

Memory 120 may be configured to store, for example, monitored physiological parameter values, such as blood pressure values, oxygen saturation values, peripheral oxygen saturation values, or any combination thereof. Memory 120 may also be configured to store calibration data that is periodically collected by CNIBP monitoring device 100.

In some examples, memory 120 may store program instructions, such as neural network algorithms. The program instructions may include one or more program modules that are executable by processing circuitry 110. For example, memory 120 may store continuous non-invasive blood pressure (CNIBP) model 124, which may be a model trained via machine learning to continuously and non-invasively determine the blood pressure of patient 101. When executed by processing circuitry 110, such program instructions, such as program instructions of CNIBP model 124, may cause processing circuitry 110 to provide the functionality ascribed to it herein. The program instructions may be embodied in software, firmware, and/or RAMware. Memory 120 may include any one or more of volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

User interface 130 may include a display 132, an input device 134, and a speaker 136. In some examples, user interface 130 may include fewer or additional components. User interface 130 is configured to present information to a user (e.g., a clinician). For example, user interface 130 and/or display 132 may include a monitor, cathode ray tube display, a flat panel display such as a liquid crystal (LCD) display, a plasma display, a light emitting diode (LED) display, and/or any other suitable display. In some examples, user interface 130 may be part of a multiparameter monitor (MPM) or other physiological signal monitor used in a clinical or other setting, a personal digital assistant, mobile phone, tablet computer, laptop computer, any other suitable computing device, or any combination thereof, with a built-in display or a separate display.

In some examples, processing circuitry 110 may be configured to present, by user interface 130, such as display 132, a graphical user interface to a user. The graphical user interface may include indications of values of one or more physiological parameters of a patient, such as, for example, blood pressure values, oxygen saturation values, information about an autoregulation status (e.g., cerebral autoregulation status), pulse rate information, respiration rate information, other patient physiological parameters, or combinations thereof via display 132. User interface 130 may also include means for projecting audio to a user, such as speaker 136.

In some examples, processing circuitry 110 may also receive input signals from additional sources (not shown), such as a user. For example, processing circuitry 110 may receive from input device 134, such as a keyboard, a mouse, a touch screen, buttons, switches, a microphone, a joystick, a touch pad, or any other suitable input device or combination of input devices, an input signal. The input signal may contain information about patient 101, such as physiological parameters, treatments provided to patient 101, or the like. Additional input signals may be used by processing circuitry 110 in any of the determinations or operations it performs in accordance with processing circuitry 110.

In some examples, if processing circuitry 110 determines that the status of patient 101 is abnormal, then processing circuitry 110 may present a notification indicating the abnormal status. The notification may include a visual, audible, tactile, or somatosensory notification (e.g., an alarm signal) indicative of the abnormal status. In some examples, processing circuitry 110 and user interface 130 may be part of the same device or supported within one housing (e.g., a computer or monitor). In other examples, processing circuitry 110 and user interface 130 may be separate devices configured to communicate through a wired connection or a wireless connection.

Sensing circuitry 140 and 142 is configured to receive signals ("physiological signals") indicative of physiological parameters from respective sensing devices 150 and 152 and communicate the physiological signals to processing circuitry 110. Sensing devices 150 and 152 may include any sensing hardware configured to sense a physiological parameter of a patient, such as, but not limited to, one or more electrodes, optical receivers, blood pressure cuffs, or the like. The sensed physiological signals may include signals indicative of physiological parameters from a patient, such as, but not limited to, blood pressure, blood oxygen saturation (e.g., pulse oximetry and/or regional oxygen saturation), blood volume, heart rate, and respiration. For example, sensing circuitry 140 and 142 may include, but are not limited to, blood pressure sensing circuitry, blood oxygen saturation sensing circuitry, blood volume sensing circuitry, heart rate sensing circuitry, temperature sensing circuitry, electrocardiography (ECG) sensing circuitry, electroencephalogram (EEG) sensing circuitry, or any combination thereof.

In some examples, sensing circuitry 140 and 142 and/or processing circuitry 110 may include signal processing circuitry 112 configured to perform any suitable analog conditioning of the sensed physiological signals. For example, sensing circuitry 140 and 142 may communicate to processing circuitry 110 an unaltered (e.g., raw) signal. Processing circuitry 110, e.g., signal processing circuitry 112, may be configured to modify a raw signal to a usable signal by, for example, filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof. In some examples, the conditioned analog signals may be processed by an analog-to-digital converter of signal processing circuitry 112 to convert the conditioned analog signals into digital signals. In some examples, signal processing circuitry 112 may operate on the analog or digital form of the signals to separate out different components of the signals. In some examples, signal processing circuitry 112 may perform any suitable digital conditioning of the converted digital signals, such as low pass, high pass, band pass, notch, averaging, or any other suitable filtering, amplifying, performing an operation on the signal, performing any other suitable digital conditioning, or any combination thereof. In some examples, signal processing circuitry 112 may decrease the number of samples in the digital detector signals. In some examples, signal processing circuitry 112 may remove dark or ambient contributions to the received signal. Additionally or alternatively, sensing circuitry 140 and 142 may include signal processing circuitry 112 to modify one or more raw signals and communicate to processing circuitry 110 one or more modified signals.

Oxygen saturation sensing device 150 (also referred to herein as blood oxygen saturation sensing device 150) is configured to generate an oxygen saturation signal indicative of blood oxygen saturation within the venous, arterial, and/or capillary systems within a region of patient 101. For example, oxygen saturation sensing device 150 may include a sensor configured to non-invasively generate a plethysmography (PPG) signal. One example of such a sensor may be one or more oximetry sensors (e.g., one or more pulse oximetry sensors) placed at one or multiple locations on patient 101, such as at a fingertip of patient 101, an earlobe of patient 101, and the like.

In some examples, oxygen saturation sensing device 150 may be configured to be placed on the skin of patient 101 to determine regional oxygen saturation of a particular tissue region, e.g., the frontal cortex or another cerebral location of patient 101. Oxygen saturation sensing device 150 may include emitter 160 and detector 162. Emitter 160 may include at least two light emitting diodes (LEDs), each configured to emit at different wavelengths of light, e.g., red or near infrared light. As used herein, the term "light" may refer to energy produced by radiative sources and may include any wavelength within one or more of the ultrasound, radio, microwave, millimeter wave, infrared, visible, ultraviolet, gamma ray or X-ray electromagnetic radiation spectra. In some examples, light drive circuitry (e.g., within sensing device 150, sensing circuitry 140, control circuitry 122, and/or processing circuitry 110) may provide a light drive signal to drive emitter 160 and to cause emitter 160 to emit light. In some examples, the LEDs of emitter 160 emit light in the range of about 600 nanometers (nm) to about 1000 nm. In a particular example, one LED of emitter 160 is configured to emit light at about 730 nm and the other LED of emitter 160 is configured to emit light at about 810 nm. Other wavelengths of light may be used in other examples.

Detector 162 may include a first detection element positioned relatively "close" (e.g., proximal) to emitter 160 and a second detection element positioned relatively "far" (e.g., distal) from emitter 160. In some examples, the first detection elements and the second detection elements may be chosen to be specifically sensitive to the chosen targeted energy spectrum of emitter 160. Light intensity of multiple wavelengths may be received at both the "close" and the "far" detector 162. For example, if two wavelengths are used, the two wavelengths may be contrasted at each location and the resulting signals may be contrasted to arrive at an oxygen saturation value that pertains to additional tissue through which the light received at the "far" detector passed (tissue in addition to the tissue through which the light received by the "close" detector passed, e.g., the brain tissue), when it was transmitted through a region of a patient (e.g., a patient's cranium). In operation, light may enter detector 162 after passing through the tissue of patient 101, including skin, bone, other shallow tissue (e.g., non-cerebral tissue and shallow cerebral tissue), and/or deep tissue (e.g., deep cerebral tissue). Detector 162 may convert the intensity of the received light into an electrical signal. The light intensity may be directly related to the absorbance and/or reflectance of light in the tissue. Surface data from the skin and skull may be subtracted out, to generate an oxygen saturation signal for the target tissues over time.

Oxygen saturation sensing device 150 may provide the oxygen saturation signal to processing circuitry 110 or to any other suitable processing device for use in determining the blood pressure of patient 101. Additional example details of determining oxygen saturation based on light signals may be found in commonly assigned U.S. Pat. No. 9,861,317, which issued on Jan. 9, 2018, and is entitled "Methods and Systems for Determining Regional Blood Oxygen Saturation." One example of such an oxygen saturation signal may be a plethysmography (PPG) signal.

In operation, blood pressure sensing device 152 and oxygen saturation sensing device 150 may each be placed on the same or different parts of the body of patient 101. For example, blood pressure sensing device 152 and oxygen saturation sensing device 150 may be physically separate from each other and may be separately placed on patient 101. As another example, blood pressure sensing device 152 and oxygen saturation sensing device 150 may in some cases be supported by a single sensor housing. One or both of blood pressure sensing device 152 or oxygen saturation sensing device 150 may be further configured to measure other parameters, such as hemoglobin, respiratory rate, respiratory effort, heart rate, saturation pattern detection, response to stimulus such as bispectral index (BIS) or electromyography (EMG) response to electrical stimulus, or the like. While an example CNIBP monitoring device 100 is shown in FIG. 1, the components illustrated in FIG. 1 are not intended to be limiting. Additional or alternative components and/or implementations may be used in other examples.

Blood pressure sensing device 152 is configured to generate a blood pressure signal indicative of a blood pressure of patient 101. For example, blood pressure sensing device 152 may include a blood pressure cuff configured to non-invasively sense blood pressure or an arterial line configured to invasively monitoring blood pressure in an artery of patient 101. In some examples, the blood pressure signal may include at least a portion of a waveform of the acquisition blood pressure. Blood pressure sensing device 152 may be configured to generate a blood pressure signal indicative of the blood pressure of patient over time. Blood pressure sensing device 152 may provide the blood pressure signal to sensing circuitry 142, processing circuitry 110, or to any other suitable processing device, which may be part of device 100 or a device separate from device 100, such as another device co-located with device 100 or remotely located relative to device 100.

Processing circuitry 110 may be configured to receive one or more signals generated by sensing devices 150 and 152 and sensing circuitry 140 and 142. The physiological signals may include a signal indicating blood pressure and/or a signal, such as a PPG signal, indicating oxygen saturation. Processing circuitry 110 may be configured to determine a blood pressure value based on the blood pressure signal.

In accordance with aspects of the present disclosure, CNIBP monitoring device 100 is configured to provide continuous non-invasive blood pressure monitoring of patient 101. To that end, CNIBP monitoring device 100 may be configured to periodically determine the blood pressure of patient 101 by periodically receiving on the blood pressure of patient 101 from blood pressure sensing device 152, such as every minute, every five minutes, every 15 minutes, and the like. For example, CNBIP monitoring device 100 may periodically turn on or activate blood pressure sensing device 152 so that blood pressure monitoring device 152 may measure the blood pressure of patient 101. In another example, blood pressure monitoring device 152 may continually monitor the blood pressure of patient 101, and CNIBP monitoring device 100 may periodically request the blood pressure of patient 101 from blood pressure monitoring device 152.

To provide continuous non-invasive blood pressure monitoring of patient 101 in the time periods between the periodic measurement of the blood pressure of patient 101 using blood pressure sensing device 152, processing circuitry 110 may be configured to derive the blood pressure of patient 101 using CNIBP model 124 based at least in part on the PPG signals provided by oxygen saturation sensing device 150 during such time periods.

Each time CNIBP monitoring device 100 uses blood pressure sensing device 152 to determine the blood pressure of patient 101 during the continuous non-invasive blood pressure monitoring of patient 101 is referred to herein as a calibration point because CNIBP monitoring device 100 is calibrated at each calibration point with the actual blood pressure of patient 101 as measured using blood pressure sensing device 152. During each calibration point, processing circuitry 110 may be configured to determine calibration data that is used to calibrate CNIBP model 124. A calibration point may periodically occur, such as every 3 minutes, every 5 minutes, every 10 minutes, every 15 minutes, every 20 minutes, and the like, and each calibration point may last a specified time period, such as the duration of one or more cardiac cycles, a specified number of seconds (e.g., 1 second, 5 seconds, etc.), and the like.

For example, at each calibration point, control circuitry 114 may be configured to send one or more timing control signals to sensing circuitry 140 and 142 to turn on, activate, or otherwise receive data from respective sensing devices 150 and 152 to collect calibration data using sensing devices 150 and 152. Blood pressure sensing device 152 may provide a blood pressure signal indicative of the blood pressure of patient 101 at the calibration point to processing circuitry 110. Similarly, oxygen saturation sensing device 150 may provide an oxygen saturation signal in the form of a PPG signal at the calibration point to processing circuitry 110. Processing circuitry 110 may operate to extract features, such as the values to a set of metrics, from the PPG signal. For example, the features may include the values of any combination of metrics such as one or more of a PPG pulse duration, a PPG relative position of a maximum upslope of a systolic rise, a PPG peak location and amplitude, a PPG perfusion index, a PPG baseline trend, a PPG respiratory cycle information (e.g., respiratory rate), a PPG upstroke area, a PPG downstroke area, a maximum gradient of a PPG upslope, and a PPG baseline value. The blood pressure of patient 101 and the features extracted from the PPG signal may form the calibration data collected by processing circuitry 110. A calibration point may be a specified period of time, such as the time period of a single cardiac cycle, one second, or any other suitable time period. As such, the features extracted from the PPG signal may include, for each feature, a sequence of values over the time period of the calibration point. For example, the PPG pulse duration may be a sequence of PPG pulse duration values over the time period of the calibration point, the PPG upstroke area may be a sequence of PPG upstroke area values over the time period, and the like.

Processing circuitry 110 may store the calibration data in memory 120. Because CNIBP monitoring device 100 is configured to periodically calibrate itself by determining the blood pressure of patient 101 using blood pressure sensing device 152, the calibration point occurs periodically, and CNIBP monitoring device 100 may be configured to determine calibration data each time CNIBP monitoring device 100 calibrates itself, via the techniques described above. In some examples, processing circuitry 110 may be configured to overwrite the calibration data stored in memory 120 with the most recently determined calibration data, so that only the most recently determined calibration data at the most recent calibration point is stored in memory 120. In other examples, processing circuitry 110 may be configured to store calibration data determined from multiple previous calibration points in memory 120.

As discussed above, in between the periodic occurrence of calibration points, CNIBP monitoring device 100 may be configured to determine the continuous non-invasive blood pressure of patient 101 by using CNIBP model 124 without using blood pressure sensing device 152 to determine the blood pressure of patient 101. In some examples, CNIBP model 124 is a neural network algorithm trained via machine learning to take the PPG signal of the patient, such as patient 101, at the current time and the calibration data determined at the most recent calibration point as inputs to determine the blood pressure of the patient at the current time.

A neural network algorithm, or artificial neural network, may include a trainable or adaptive algorithm utilizing nodes that define rules. For example, a respective node of a plurality of nodes may utilize a function, such as a non-linear function or if-then rules, to generate an output based on an input. A respective node of the plurality of nodes may be connected to one or more different nodes of the plurality of nodes along an edge, such that the output of the respective node includes the input of the different node. The functions may include parameters that may be determined or adjusted using a training set of inputs and desired outputs, such as, for example, a predetermined association between one or more PPG signals sensed from patient 101 or a population of patients and one or more second blood pressures of patient 101 or a population of patients measured contemporaneously with the PPG signal, along with a learning rule, such as a back-propagation learning rule. The back-propagation learning rule may utilize one or more error measurement comparing the desired output to the output produced by the neural network algorithm to train the neural network algorithm by varying the parameters to minimize the one or more error measurements.

An example neural network includes a plurality of nodes, at least some of the nodes having node parameters. An input including at least the PPG signal generated by oxygen saturation sensing device 150 or oxygen saturation sensing circuitry 140 and indicative of a blood oxygen saturation of patient 101 may be input to a first node of the neural network algorithm. In some examples, the input may include a plurality of inputs, each input into a respective node. The first node may include a function configured to determine an output based on the input and one or more adjustable node parameters. In some examples, the neural network may include a propagation function configured to determine an input to a subsequent node based on the output of a preceding node and a bias value. In some examples, a learning rule may be configured to modify one or more node parameters to produce a favored output. For example, the favored output may be constrained by one or more threshold values and/or to minimize one or more error measurements. The favored output may include an output of a single node, a set of nodes, or the plurality of nodes.

The neural network algorithm may iteratively modify the node parameters until the output includes the favored output. In this way, processing circuitry 110 may be configured to iteratively evaluating outputs of the neural network algorithm and iteratively modifying at least one of the node parameters based on the evaluation of the outputs of the neural network algorithm to determine the blood pressure of a patient, such as patient 101, based on the modified neural network algorithm. In some examples, a neural network algorithm may enable processing circuitry 110 to more accurately determine the continuous blood pressure of patient 101 using features extracted from a PPG signal along with calibration data from a most recent calibration point compared to other techniques and/or reduce computational time and/or power required to determine the altered blood pressure value.

In accordance with aspects of the present disclosure, processing circuitry 110 may be configured to execute CNIBP model 124 to continually determine the blood pressure of patient 101 between calibration points. At any particular time t between calibration points, processing circuitry 110 may be configured to use CNIBP model 124 to determine the blood pressure of patient 101 at time t. At time t, processing circuitry 110 may be configured to receive a PPG signal of patient 101 from oxygen saturation sensing device 150. Processing circuitry 110 may input the PPG signal of patient 101 at time t along with the calibration data derived at the calibration point most recent to time t into CNIBP model 124, and processing circuitry 110 may be configured to execute CNIBP model 124 to determine the blood pressure of patient 101 at time t from such inputs.

Once processing circuitry 110 has determined a blood pressure for patient 101, processing circuitry 110 may provide information indicative of the continuous blood pressure of patient 101 to an output device, such as user interface 130. In some examples, under the control of processing circuitry 110, user interface 130, for example, display 132, may present a graphical user interface that includes information indicative of the continuous blood pressure of patient 101. In some examples, the indication of the blood pressure for patient 101 may include text, colors, and/or audio presented to a user. In addition to or instead of the graphical user interface, processor circuitry 110 may be configured to generate and present information indicative of the continuous blood pressure of patient 101 via speaker 136, such as by announcing, via speech, the current blood pressure of patient 101.

In some examples, CNIBP monitoring device 100, e.g., processing circuitry 110 or user interface 130, may include a communication interface to enable CNIBP monitoring device 100 to exchange information with external devices. The communication interface may include any suitable hardware, software, or both, which may allow CNIBP monitoring device 100 to communicate with electronic circuitry, a device, a network, a server or other workstations, a display, or any combination thereof. For example, processing circuitry 110 may receive blood pressure values and/or oxygen saturation values from an external device via the communication interface.

The components of CNIBP monitoring device 100 that are shown and described as separate components are shown and described as such for illustrative purposes only. In some examples the functionality of some of the components may be combined in a single component. For example, the functionality of processing circuitry 110 and control circuitry 122 may be combined in a single processor system. Additionally, in some examples the functionality of some of the components of CNIBP monitoring device 100 shown and described herein may be divided over multiple components. For example, some or all of the functionality of control circuitry 122 may be performed in processing circuitry 110, or sensing circuitry 140 and 142. In other examples, the functionality of one or more of the components may be performed in a different order or may not be required.

Figure 2:
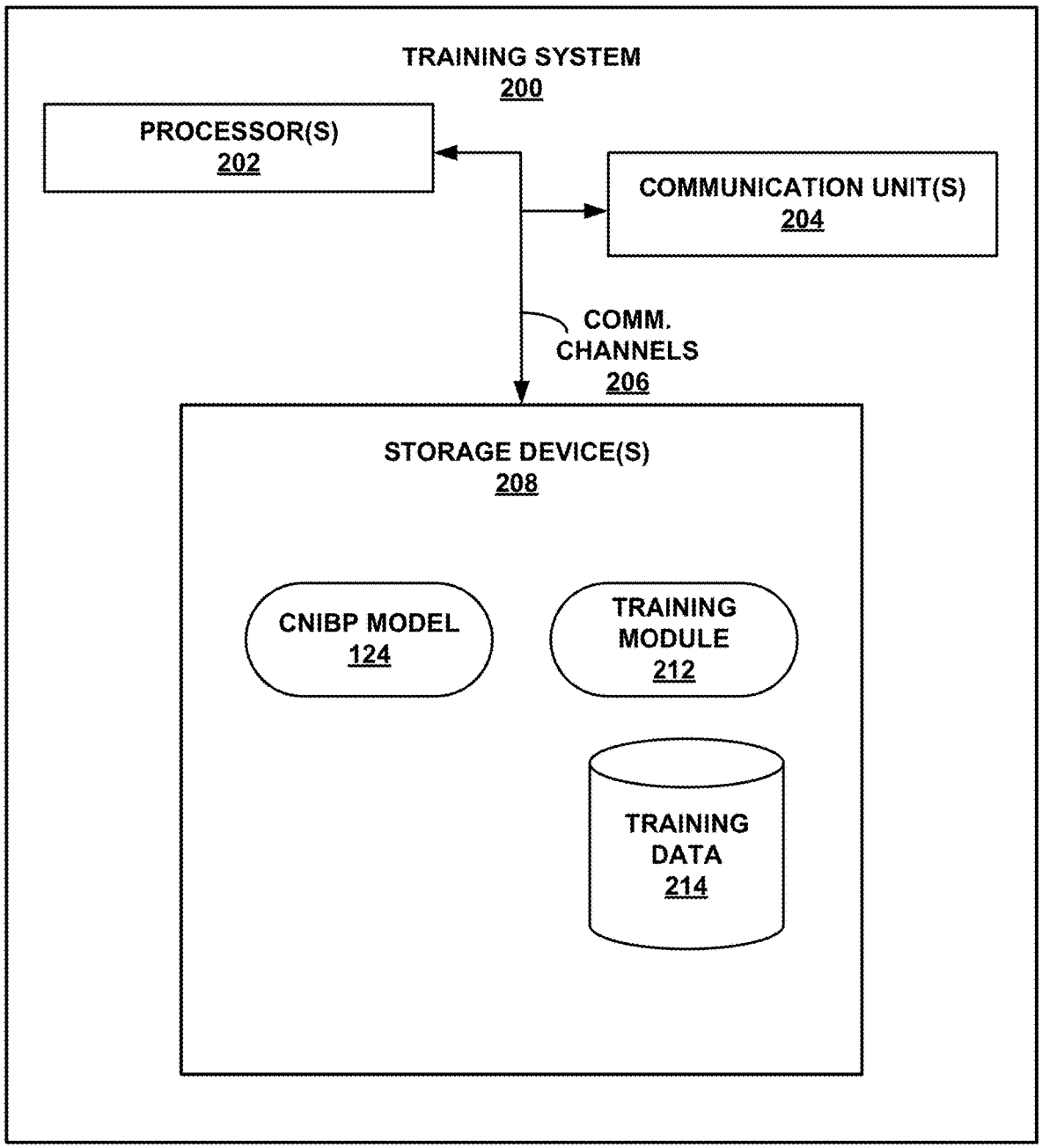
FIG. 2 illustrates details of an example training system 200 that may perform training of a CNIBP model used by the CNIBP device shown in FIG. 1.

FIG. 2 illustrates details of an example training system 200 that may perform training of CNIBP model 124 shown in FIG. 1. FIG. 2 illustrates only one particular example of training system 200, and many other example devices having more, fewer, or different components may also be configurable to perform operations in accordance with techniques of the present disclosure.

While displayed as part of a single device in the example of FIG. 2, components of training system 200 may, in some examples, be located within and/or be a part of different devices. For instance, in some examples, training system 200 may represent a "cloud" computing system. Thus, in these examples, the modules illustrated in FIG. 2 may span across multiple computing devices. In some examples, training system 200 may represent one of a plurality of servers making up a server cluster for a "cloud" computing system. In other examples, training system 200 may be an example of CNIBP monitoring device 100 shown in FIG. 1.

As shown in the example of FIG. 2, training system 200 includes one or more processors 202, one or more communications units 204, and one or more storage devices 208. Storage devices 208 further include CNIBP model 124, training module 212, and training data 214. Each of components 202, 204, and 208 may be interconnected (physically, communicatively, and/or operatively) for inter-component communications. In the example of FIG. 2, components 202, 204, and 208 may be coupled by one or more communications channels 206. In some examples, communications channels 206 may include a system bus, network connection, inter-process communication data structure, or any other channel for communicating data. CNIBP model 124, training module 212, and training data 214 may also communicate information with one another as well as with other components in training system 200.

In the example of FIG. 2, one or more processors 202 may implement functionality and/or execute instructions within training system 200. For example, one or more processors 202 may receive and execute instructions stored by storage devices 208 that execute the functionality of training module 212. These instructions executed by one or more processors 202 may cause training system 200 to store information within storage devices 208 during execution. One or more processors 202 may execute instructions of training module 212 to train CNIBP model 124 using training data 214. That is, training module 212 may be operable by one or more processors 202 to perform various actions or functions of training system 200 described herein.

In the example of FIG. 2, one or more communication units 204 may be operable to communicate with external devices via one or more networks by transmitting and/or receiving network signals on the one or more networks. For example, training system 200 may use communication units 204 to transmit and/or receive radio signals on a radio network such as a cellular radio network. Likewise, communication units 204 may transmit and/or receive satellite signals on a satellite network such as a global positioning system (GPS) network. Examples of communication units 204 include a network interface card (e.g. such as an Ethernet card), an optical transceiver, a radio frequency transceiver, or any other type of device that can send and/or receive information. Other examples of communication units 204 may include Near-Field Communications (NFC) units, Bluetooth® radios, short wave radios, cellular data radios, wireless network (e.g., Wi-Fi®) radios, as well as universal serial bus (USB) controllers.

One or more storage devices 208 may be operable, in the example of FIG. 2, to store information for processing during operation of training system 200. In some examples, storage devices 208 may represent temporary memory, meaning that a primary purpose of storage devices 208 is not long-term storage. For instance, storage devices 208 of training system 200 may be volatile memory, configured for short-term storage of information, and therefore not retain stored contents if powered off. Examples of volatile memories include random access memories (RAM), dynamic random access memories (DRAM), static random access memories (SRAM), and other forms of volatile memories known in the art.

Storage devices 208, in some examples, also represent one or more computer-readable storage media. That is, storage devices 208 may be configured to store larger amounts of information than a temporary memory. For instance, storage devices 46 may include non-volatile memory that retains information through power on/off cycles. Examples of non-volatile memories include magnetic hard discs, optical discs, floppy discs, flash memories, or forms of electrically programmable memories (EPROM) or electrically erasable and programmable (EEPROM) memories. In any case, storage devices 208 may, in the example of FIG. 2, store program instructions and/or data associated with CNIBP model 124, training module 212, and training data 214.

Training system 200 may, in the example of FIG. 2, execute training module 212 to train CNIBP model 124 using training data 214 to more accurately determine the blood pressure of a patient between periodic calibration points by training CNIBP model 124 to associate one or more PPG morphological feature sequences with respective blood pressure values. CNIBP model 124 may include a deep learning architecture such as a recurrent neural network, convolutional neural network, and the like that includes multiple layers to progressively extract higher level features from inputs to CNIBP model 124.

In some examples, training module 212 trains CNIBP model 124 to use, as inputs, a PPG signal received at time t from sensing circuitry 140 and oxygen saturation sensing device 150 (FIG. 1) coupled to patient 101, the calibration data determined at the most recent calibration point to time t, and an elapsed time at time t since the most recent calibration point to determine the blood pressure of patient 101 at time t. The calibration data may include, for example, the blood pressure of patient 101 as measured by BP sensing circuitry 142 and blood pressure sensing device 152 (FIG. 1) at the most recent calibration point and values of a set of metrics derived from a PPG signal received from oxygen saturation sensing device 150 at the most recent calibration point.

In some examples, training data 214 used to train CNIBP model 124 includes data from only patient 101 and from no other subjects. In other examples, training data 214 may include data from a population of patients, such as sets of calibration data at most recent calibration points of a population of patients, sets of elapsed time since the most recent calibration points, sets of PPG signals of the population of patients, and sets of target blood pressure values of the population of patients. For example, each individual piece of training data in training data 214 may be an association of a target blood pressure for a patient at time t, the values of a set of metrics derived from a PPG signal received from the patient at time t, the values of a set of metrics derived from a PPG signal received from the patient at a most recent calibration time to time t, the blood pressure of the patient as measured at the most recent calibration time to time t, and the elapsed time at time t since the most recent calibration time.

In some examples, once training module 212 has trained CNIBP model 124 using training data 214, training module 212 may test CNIBP model 124 by using a set of test data not yet encountered by CNIBP model 124 to determine how closely the blood pressures determined by CNIBP model 124 based on the test data matches the expected target blood pressures of the test data. In this way, training module 212 may evaluate and further refine CNIBP model 124.

When training module 212 has completed training of CNIBP model 124, CNIBP model 124 can be installed, uploaded, or otherwise transferred to CNIBP monitoring device 100. In some examples, training module 212 may upload or otherwise transfer a copy of CNIBP model 124 to another server or to the cloud, and CNIBP monitoring device 100 may use CNIBP model 124 via a network such as the Internet, a virtual private network, a local area network, and the like.

FIGS. 3A and 3B illustrate an example divergence of blood pressure measurements and PPG signals. Such divergence may be potentially ameliorated by the techniques disclosed herein. As shown in FIG. 3A, graph 300A includes blood pressure signal 302A taken of a patient using an invasive arterial line while graph 300B includes a PPG signal 302B taken of the same patient using a pulse oximeter at about the same time as blood pressure signal 302A in graph 300A. Similarly, as shown in graph 300B, graph 300C includes blood pressure signal 302C taken of a patient using an invasive arterial line while graph 300D includes a PPG signal 302D taken of the same patient using a pulse oximeter at about the same time as blood pressure signal 302C in graph 300C. While FIG. 3A shows that PPG signal 302B is similar to blood pressure signal 302A in morphology, FIG. 3B shows that PPG signal 302D is very different from blood pressure signal 302C in morphology.

As can be seen, it may be difficult to accurately map PPG signals to blood pressure signals. This may be due to numerous confounders such as the influence of one or more of: contact force, ambient temperature, drugs, vasomotion, movement, arterial stiffening, posture changes, or the like. Due to such confounders, a continuous non-invasive blood pressure monitoring algorithm may lose its accuracy over time.

A technique to address a continuous non-invasive blood pressure monitoring algorithm that may lose its accuracy over time includes periodically calibrating the continuous non-invasive blood pressure monitoring algorithm with the blood pressure as measured by a non-invasive blood pressure monitoring system, such as an inflatable cuff-type blood pressure monitoring system.

FIG. 4 illustrates example graph 400 of blood pressure over time as determined using a continuous non-invasive blood pressure monitoring algorithm that is periodically calibrated with the blood pressure as measured by a non-invasive blood pressure monitoring system. As shown in FIG. 4, a CNIBP monitoring system can periodically calibrate blood pressure 402 as determined using a continuous non-invasive blood pressure monitoring algorithm with the blood pressure as measured by a non-invasive blood pressure monitoring system, such as at times $t_0$, $t_1$, and $t_2$, which are referred to throughout this disclosure as calibration points.

At time $t_0$, the CNIBP monitoring system calibrates blood pressure 402 with the blood pressure 404A as measured at time $t_0$ by the CNIBP monitoring system. After blood pressure 402 is calibrated at time $t_0$, the CNIBP monitoring system determines blood pressure 402 using the continuous non-invasive blood pressure monitoring algorithm until reaching time $t_1$. At time $t_1$, CNIBP monitoring system calibrates blood pressure 402 with the blood pressure 404B as measured at time $t_1$ by the CNIBP monitoring system. After blood pressure 402 is calibrated at times $t_1$, CNIBP monitoring system determines blood pressure 402 using the continuous non-invasive blood pressure monitoring algorithm until reaching time $t_2$. At time $t_2$, CNIBP monitoring system determines calibrates blood pressure 402 with the blood pressure 404C as measured at time $t_2$ by the CNIBP monitoring system. After blood pressure 402 is calibrated at times $t_2$, CNIBP monitoring system determines blood pressure 402 using the continuous non-invasive blood pressure monitoring algorithm until the next calibration point is reached.

As can be seen in FIG. 4, blood pressure 402 determined using a continuous non-invasive blood pressure monitoring algorithm may drift significantly (e.g., a way that may meaningfully impact the value of the blood pressure monitoring) from the blood pressure measured by a non-invasive blood pressure monitoring system. For example, there may be a significant difference between blood pressure 402 determined using a continuous non-invasive blood pressure monitoring algorithm at time $t_1$ compared with the blood pressure 404B as measured time $t_1$ by the non-invasive blood pressure monitoring system.

One technique for compensating for the such a difference includes adding or subtracting the difference between the blood pressure determined using a continuous non-invasive blood pressure monitoring algorithm and the blood pressure measured by a non-invasive blood pressure monitoring system at the most recent calibration point. For example, because blood pressure 402 determined at time $t_1$ using a continuous non-invasive blood pressure monitoring algorithm is higher than the blood pressure 404B as measured at time $t_1$ by the non-invasive blood pressure monitoring system, an instant blood pressure 402 that is determined between times $t_1$ and $t_2$ may be adjusted by subtracting, from the instant blood pressure 402 that is determined between times $t_1$ and $t_2$, the difference between blood pressure 402 determined at time $t_1$ using a continuous non-invasive blood pressure monitoring algorithm and the blood pressure 404B as measured at time $t_1$ by the non-invasive blood pressure monitoring system.

In accordance with aspects of the present disclosure, CNIBP monitoring device 100 is configured to use CNIBP model 124 to potentially more accurately determine the blood pressure of a patient between calibration points. For example, CNIBP monitoring device 100 may determine, at each calibration point, such as at time $t_0$, time $t_1$, and time $t_2$, CNIBP monitoring device 100 may determine calibration data that may include the blood pressure measured at the calibration point and values of a set of metrics derived from a PPG signal received at the calibration point. To determine the blood pressure of the patient at a time between calibration points, such as at time $t_3$, CNIBP model 124 may input the values of a set of metrics determined at time $t_3$, the calibration data determined at time $t_0$, and the elapsed time at time $t_3$ since the most recent calibration point at time $t_0$ into CNIBP model 124 to determine the blood pressure of the patient at time $t_3$.

Figure 5:
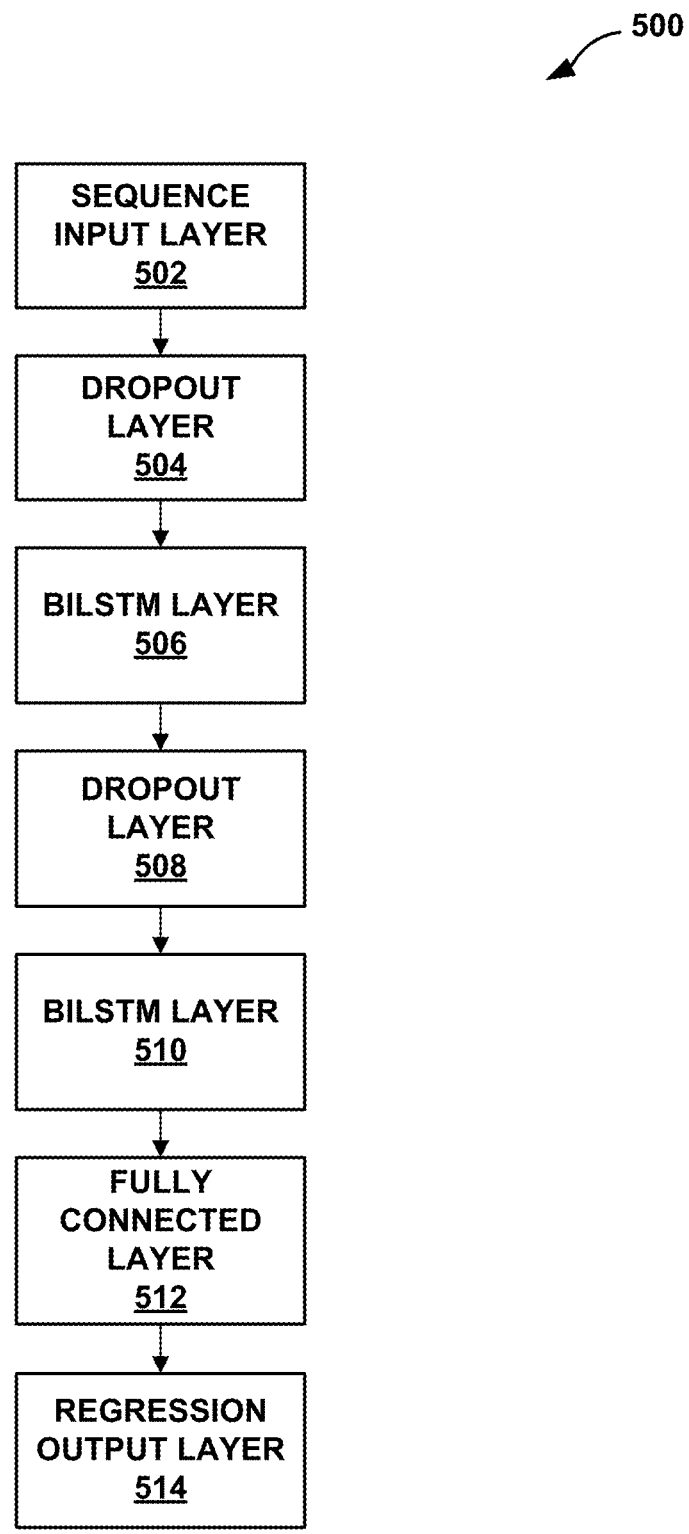
FIG. 5 illustrates an example deep learning architecture of the CNIBP model of FIGS. 1 and 2.

FIG. 5 illustrates an example deep learning architecture 500 of CNIBP model 124. While deep learning architecture 500 is illustrated in FIG. 5 as being a long short-term memory (LSTM) deep learning architecture that is used to train a LSTM model, any other deep learning architectures may equally be suitable for training CNIBP model 124.

As shown in FIG. 5, deep learning architecture 500 may include sequence input layer 502, dropout layer 504, bidirectional long short-term memory (BiLSTM) layer 506, dropout layer 508, BiLSTM layer 510, fully connected layer 512, and regression output layer 514. Sequence input layer 502 may be connected to dropout layer 504. Dropout layer 504 may be connected to BiLSTM layer 506. BiLSTM layer

506 may be connected to dropout layer 508. Dropout layer 508 may be connected to BiLSTM layer 510, BiLSTM layer 510 may be connected to fully connected layer 512. Fully connected layer 512 may be connected to regression output layer 514.

A sequence input layer such as sequence input layer 502 inputs sequence data to a neural network. Thus, sequence input layer 502 receives features that are used to train deep learning architecture 500, which include values of a set of metrics derived from a PPG signal, the calibration data determined at the most recent calibration point, and the elapsed time since the most recent calibration point. The features received by sequence input layer 502 are described in detail below with respect to FIGS. 6A and 6B.

A dropout layer such as dropout layer 504 and dropout layer 508 randomly sets input elements to zero with a given probability. By randomly setting input elements to zero, a dropout layer may enable elements to be ignored during the training phase. Selectively ignoring elements during the training phase may prevent over-fitting of training data.

A BiLSTM layer such as BiLSTM layer 506 and BiLSTM layer 510 learns bidirectional long-term dependencies between time steps of time series or sequence data. These dependencies may be useful for the network to learn from a complete time series at each time step.

A fully connected layer such as fully connected layer 512 multiplies the input (e.g., from BiLSTM layer 510) by a weight matrix and then adds a bias vector. A regression output layer such as regression output layer 514 computes the half-mean-squared-error loss for regression problems and outputs a predicted response of the trained regression network as a result of training CNIBP model 124 having deep learning architecture 500.

To train CNIBP model 124, training system 200 (FIG. 2) may derive a set of features and associated target values and may input the features and the associated target values into CNIBP model 124 to train CNIBP model 124 to estimate target values based on the inputted features. For example, to train CNIBP model 124 to predict the blood pressure of patient 101 from a PPG signal of patient 101 (and without actually measuring the blood pressure using a blood pressure monitoring device, such as an inflatable cuff-type blood pressure monitoring system or an arterial line), training system 200 may extract features from the PPG signal of patient 101 or from PPG signals of one or more other patients/subjects and may use such features along with associated target blood pressures to train CNIBP model 124 to predict blood pressure values of patient 101 from the features of the PPG signals.

For example, training system 200 may pair up a timeseries of features extracted from the PPG signal of a patient, such as PPG signals received from the patient from a pulse oximeter, with an associated target blood pressure, such as a systolic pressure (SP), diastolic pressure (DP), mean arterial pressure (MAP), pulse pressure (PP), and the like of the patient. Training system 200 may input such pairs of features extracted from PPG signals and target blood pressures from a population of patients to train CNIBP model 124 to associate the PPG morphological feature sequences with the blood pressure values.

By training CNIBP model 124, CNIBP model 124 may be able to receive, as input, a timeseries of features extracted from the PPG signal of patient 101, and may determine a blood pressure value for the patient based on the inputted features. Training system 200 may test the CNIBP model 124 by using a test set of PPG feature sequences that the model has not yet encountered to determine the associated blood pressures. Training system 200 may input the test set of PPG feature sequences into the CNIBP model 124 and may compare the blood pressure values outputted by the CNIBP model 124 against the expected target blood pressure values for the test set of PPG feature sequences to evaluate and further refine the CNIBP model 124.

Figure 6A:
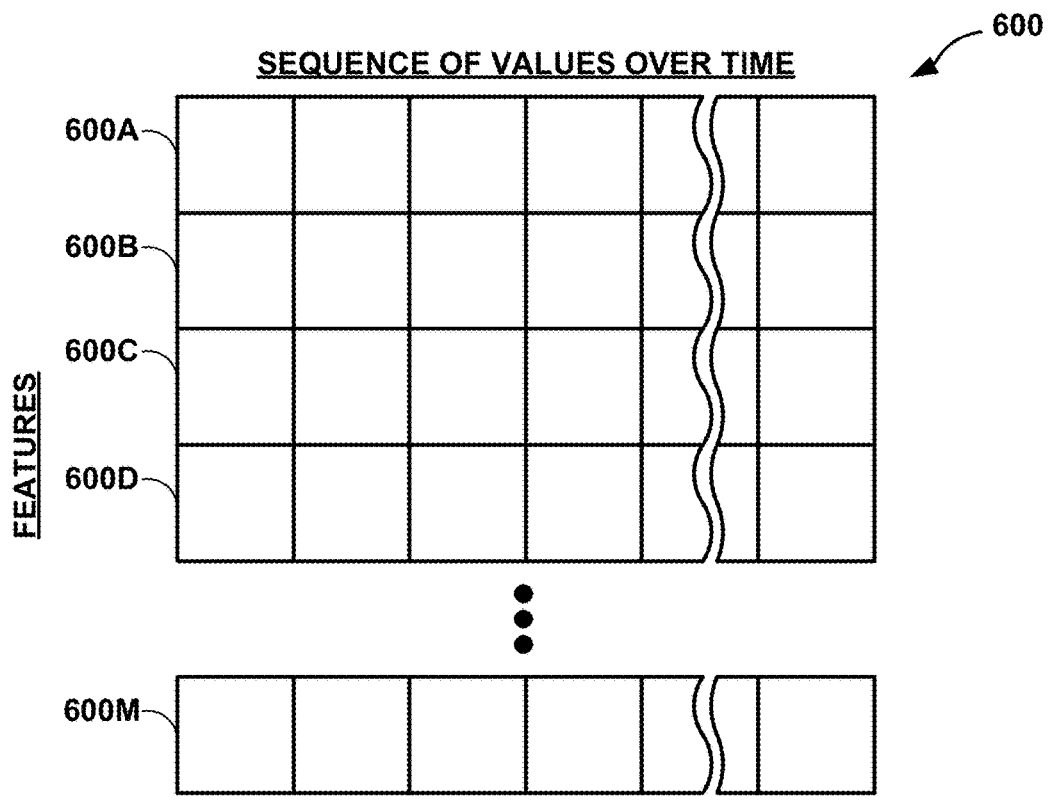
FIGS. 6A and 6B illustrate example features that may be used to train the example CNIBP model of FIGS. 1 and 2.
Figure 6B:
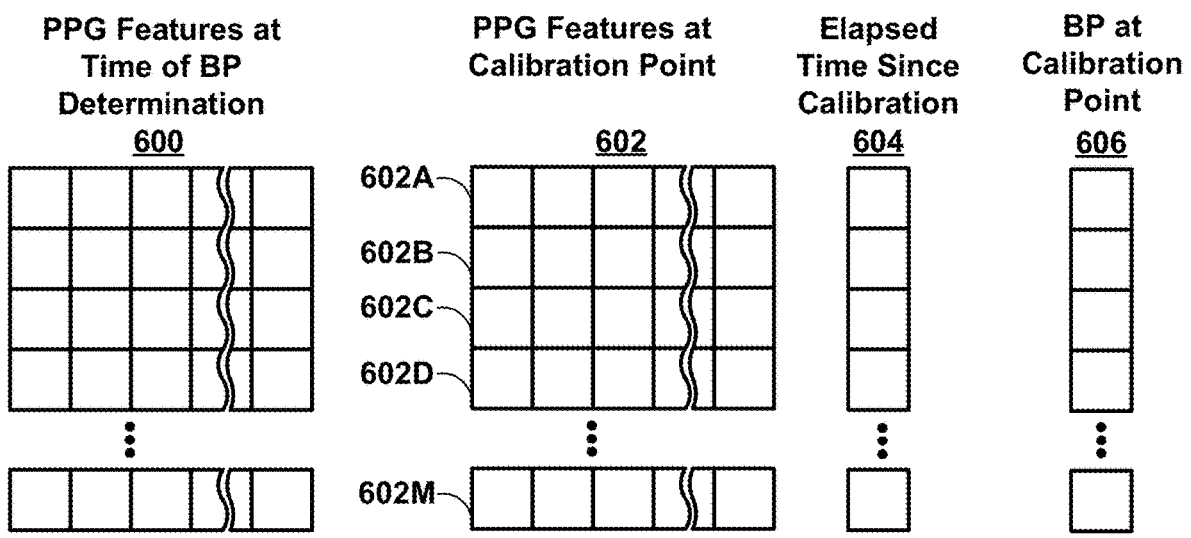

FIGS. 6A and 6B illustrate example features that may be used to train the example CNIBP model 124 of FIGS. 1 and 2. As shown in FIG. 6A, features 600 may be an example set of features from a PPG signal that are used to train CNIBP model 124, as discussed above. Similarly, features 600 may also be an example of inputs into a CNIBP model 124 from which the CNIBP model 124 may determine a blood pressure of patient 101 (without actually measuring the blood pressure using a blood pressure monitoring device, such as an inflatable cuff-type blood pressure monitoring system or an arterial line).

Features 600 may be values of a set of metrics derived from a PPG signal over a specific time period. For example, features 600 may include features 600A-600M that may include any combination of metrics derived from a PPG signal, such as a PPG pulse duration, a PPG relative position of a maximum upslope of a systolic rise, a PPG peak location and amplitude, a PPG perfusion index, a PPG baseline trend, a PPG respiratory cycle information, a PPG upstroke area, a PPG downstroke area, a maximum gradient of a PPG upslope, and a PPG baseline value.

Each of features 600A-600M may include a sequence of values over time for a specific metric derived from the PPG signal. For example, feature 600A may include a sequence of values for the PPG upstroke area, feature 600B may include a sequence of values for the PPG downstroke area, feature 600C may include a sequence of values for the PPG amplitude, feature 600D may include a sequence of values for the PPG maximum upslope, and the like.

The sequence of values over time may be a sequence of values over a specified time period, such as 5 seconds, 10 seconds, 20 seconds, and the like. In some examples, the specified time period may be the entire time period that has elapsed since the most recent occurrence of the calibration point, while in other examples the specified time period may be the prior 5 seconds, 10 seconds, 20 seconds, and the like. Because each of features 600A-600M includes a sequence of values over a time period for a specific metric, each of features 600A-600M may be a feature vector of a sequence of values over a time period, and features 600 as a whole may be referred to as a feature matrix made up of feature vectors (e.g., features 600A-600M).

In some examples, over the time period, the sequence of values of features 600A-600M may be calculated over the cardiac cycles of patient 101, such that each value of a sequence of values of features 600A-600M may be a value taken over a different cardiac cycle of patient 101 during the time period. In some examples, over the time period, the sequence of values of features 600A-600M may be calculated over a specified time interval, such as 1 second, 2 seconds, and the like, such that the sequence of values of features 600A-600M may be a value taken over a sequence of such time intervals within the time period.

In further examples, over the time period, a value of a sequence of values may be taken at a single point in time, such as on a single pulse, so that a sequences of values of features 600A-600M may include values taken over a sequence of points in time. For example, the value of the peak of the derivative of a pulse may be taken from a whole pulse, such as using the pulse area, so that a sequence of values may be taken over a sequence of pulses, or may be taken across a number of pulses. A value of a sequence of values may also be taken across a series of points in time, such as across a number of pulses, such as when a value is derived from a sequence of maximum derivatives taken in a sequence of pulses. Thus, in some examples, the sequence of values may vary in length based on the number of pulses, which is a function of the heart rate of patient 101, within the specified time period.

Features 600 are derived from a PPG signal indicative of blood oxygen saturation of patient 101 at the time the blood pressure of the patient is to be determined. Thus, during training of CNIBP model 124, features 600 derived from a PPG signal received from patient 101 at a particular time is paired with a target blood pressure for patient 101 at the same particular time. Similarly, feature 600 derived from a PPG signal indicative of blood oxygen saturation of patient 101 at a particular time is inputted into the machine trained model to determine the blood pressure of patient 101 at the particular time.

While training system 200 may train deep learning architecture 500 using sets of features 600 derived from PPG signals along with associated target blood pressure values, training system 200 may improve the accuracy of the machine trained model it generates by also using features derived from calibration data at the most recent calibration point to train CNIBP model 124 and by also using such features derived from calibration data as input into CNIBP model 124 to determine the blood pressures of patients. A continuous non-invasive blood pressure monitoring system, such as CNIBP monitoring device 100 may periodically determine calibration data at calibration points from a patient, such as patient 101. The features from the calibration data may include, for example, values of a set of metrics derived from a PPG signal received from the patient at the calibration point and the blood pressure of the patient at the calibration point.

As discussed in this disclosure, each time CNIBP monitoring device 100 determines calibration data from patient 101 is referred to herein as a calibration point. At each calibration point, CNIBP monitoring device 100 receives a PPG signal from an oxygen saturation sensing device 150 that measures the oxygen saturation of patient 101 and measures the blood pressure of patient 101 using blood pressure sensing device 152. CNIBP monitoring device 100 determines the values of a set of metrics from the received PPG signal, while the values of the set of metrics derived from the PPG signal as well as the measured blood pressure forms the calibration data determined at the calibration point.

Because CNIBP monitoring device 100 both receives a PPG signal from oxygen saturation sensing device 150 and measures the blood pressure of patient 101 using blood pressure sensing device 152 at each calibration point, the features of a PPG signal received from patient 101 is, in effect, mapped to an actual measured blood pressure of patient 101 at each calibration point. Thus, by using the calibration data received at the most recent calibration point as additional inputs for training CNIBP model 124, CNIBP model 124 may improve its accuracy in determining the blood pressure of patients.

As shown in FIG. 6B, features 602 and features 606 may be features extracted from a calibration point. In particular, features 602 may be values of a set of metrics derived from a PPG signal at a calibration point over a specific time period. For example, features 602 may include features 602A-602M that may include metrics derived from a PPG signal, such as any combination of a PPG pulse duration, a PPG relative position of a maximum upslope of a systolic rise, a PPG peak location and amplitude, a PPG perfusion index, a PPG baseline trend, a PPG respiratory cycle information, a PPG upstroke area, a PPG downstroke area, a maximum gradient of a PPG upslope, and a PPG baseline value.

Each of features 602A-602M may include a sequence of values over time for a specific metric derived from the PPG signal. The sequence of values over time may be a sequence of values over a specified time period, such as over a cardiac cycle. Because each of features 602A-602M includes a sequence of values over a time period for a specific metric, each of features 602A-602M may be a feature vector of a sequence of values over a time period, and features 602 as a whole may be referred to as a feature matrix made up of feature vectors (e.g., features 602A-602M).

Features 602 are similar to features 600 in that features 600 may include sequences of value over time for the same set of metrics as features 600. For example, if features 600 include a sequence of values for the PPG upstroke area, a sequence of values for the PPG downstroke area, a sequence of values for the PPG amplitude, and a sequence of values for the PPG maximum upslope, then features 600 may correspondingly also include a sequence of values for the PPG upstroke area, a sequence of values for the PPG downstroke area, a sequence of values for the PPG amplitude, and a sequence of values for the PPG maximum upslope.

Thus, features 602 and features 600 may each have the same number of feature vectors, where the feature vectors of features 602 and features 600 include sequences of values for the same set of metrics. For example, if features 600 includes 5 feature vectors containing sequences of values of five metrics, then features 602 may correspondingly also include 5 feature vectors containing sequences of values for the same five metrics.

Features 606 extracted from a calibration point may be the value of the patient's blood pressure measured at the calibration point. The blood pressure may be any one or more of a systolic pressure (SP), diastolic pressure (DP), mean arterial pressure (MAP), pulse pressure (PP), and the like of the patient measured using a non-invasive blood pressure monitoring system, such as an inflatable cuff-type blood pressure monitoring system. Features 606 may include a copy of the value of the patient's blood pressure for each feature of features 600 or features 602, so that features 606 includes as many copies of the value of the patient's blood pressure as there are features in features 600 or features 602. For example, if features 600 includes 6 feature vectors, then features 602 also includes 6 feature vectors, and features 606 includes six copies of the value of the patient's blood pressure, one for each of the features of features 600 or features 602. The six copies of the value of the patient's blood pressure may be the value of the patient's blood pressure as measured repeated six times.

Features 604 may be a value that corresponds the time elapsed since the most recent calibration point. The value may be in milliseconds, seconds, minutes, and the like. Because calibration points may occur periodically, such as every 3 minutes, every 5 minutes, every 15 minutes, every 30 minutes, every hour, every 2 hours, every 4 hours, every 8 hours, and the like, the most recent calibration point may be the calibration point that is prior to the time when processing circuitry 110 uses the CNIBP model 124 to determine a patient's blood pressure without any intervening calibration points between the calibration point and the time when processing circuitry 110 uses the CNIBP model 124 is used to determine the patient's blood pressure. For example, if after reaching a first calibration point a second calibration point is reached, and if the CNIBP model 124 is used to determine a patient's blood pressure at a specific time after the second calibration point is reached but before a third calibration point is reached, then the second calibration point is the most recent calibration point to the specific time at which the CNIBP model 124 is used to determine the patient's blood pressure.

Similar to features 606, features 604 may include a copy of the value of the time elapsed since the most recent calibration point for each feature of features 600 or features 602, so that features 604 includes as many copies of the value of the time elapsed since the most recent calibration point as there are features in features 600 or features 602. For example, if features 600 includes 6 feature vectors, then features 602 also includes 6 feature vectors, and features 604 includes six copies of the value of the time elapsed since the most recent calibration point, one for each of the features of features 600 or features 602. The six copies of the time elapsed since the most recent calibration point may be the value of the time elapsed since the most recent calibration point repeated six times.

Training system 200 may concatenate features 600, 602, 604, and 606 and use the concatenation of features 600, 602, 604, and 606 to train CINBP model 124. As described above with reference to FIG. 2, in some examples, training module 212 of training system 200 may use training data 214 from only patient 101 or from a population of patients to train CINBP model 124. Each piece of training data in training data 21 may include an association of a target blood pressure with a concatenation of features 600, 602, 604, and 606 in order to train CNIBP model 124 to determine a blood pressure based on features 600, 602, 604, and 60.

Similarly, CNIBP monitoring device 100 (e.g., processing circuitry 110) may use features 600, 602, 604, and 606 as inputs into the CNIBP model 124 to determine the blood pressure of a patient at time t. As described above, CNIBP monitoring device 100 may determine features 600 from a PPG signal received from oxygen saturation sensing device 150, such as a pulse oximeter, that is attached to the patient at time t. For example, CNIBP monitoring device 100 may determine features 600 by deriving values of a set of metrics for the patient from the PPG signal at time t.

CNIBP monitoring device 100 may also determine features 602 and features 606 from the calibration data it obtains at the calibration point most recent to time t. As described above, the calibration point most recent to time t may be the calibration point that is both prior to time t and is also most recent to time t. CNIBP monitoring device 100 may determine features 602 from a PPG signal received from oxygen saturation sensing device 150, such as a pulse oximeter, that is attached to the patient at the calibration point most recent to time t. For example, CNIBP monitoring device 100 may determine features 602 by deriving values of a set of metrics for the patient from the PPG signal at the most recent calibration point.

CNIBP monitoring device 100 may also determine features 606 as the value of a blood pressure measurement of the patient at the most recent calibration point. For example, CNIBP monitoring device 100 may measure the patient's blood pressure using a non-invasive blood pressure monitoring system, such as an inflatable cuff-type blood pressure monitoring system. CNIBP monitoring device 100 may also determine features 604 as the value of the elapsed time at time t since the most recent calibration point. For example, CNIBP monitoring device 100 may derive feature 604 by subtracting time t from the time of the most recent calibration point.

CNIBP monitoring device 100 may use the CNIBP model 124 to determine the blood pressure of the patient at time t. CNIBP monitoring device 100 may input features 600, features 602, features 604, and features 606 into the CNIBP model 124 and CNIBP model 124 may, in response, output the blood pressure of the patient at time t.

Figure 7A:
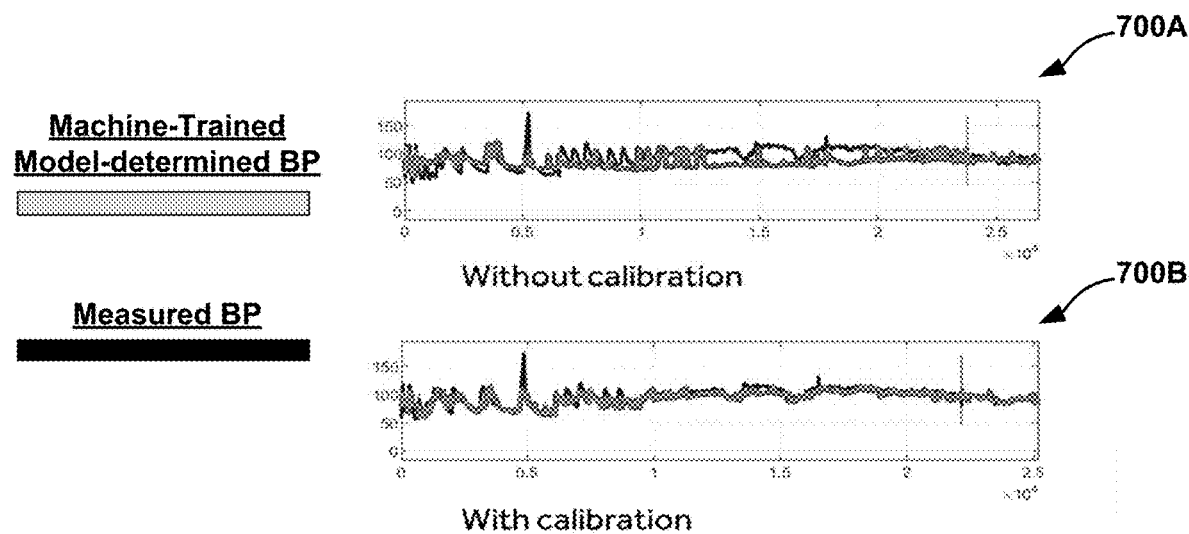
FIGS. 7A and 7B illustrate example graphs that depict the improvements in accuracy by determining the blood pressure of a patient using the CNIBP model of FIGS. 1 and 2.
Figure 7B:
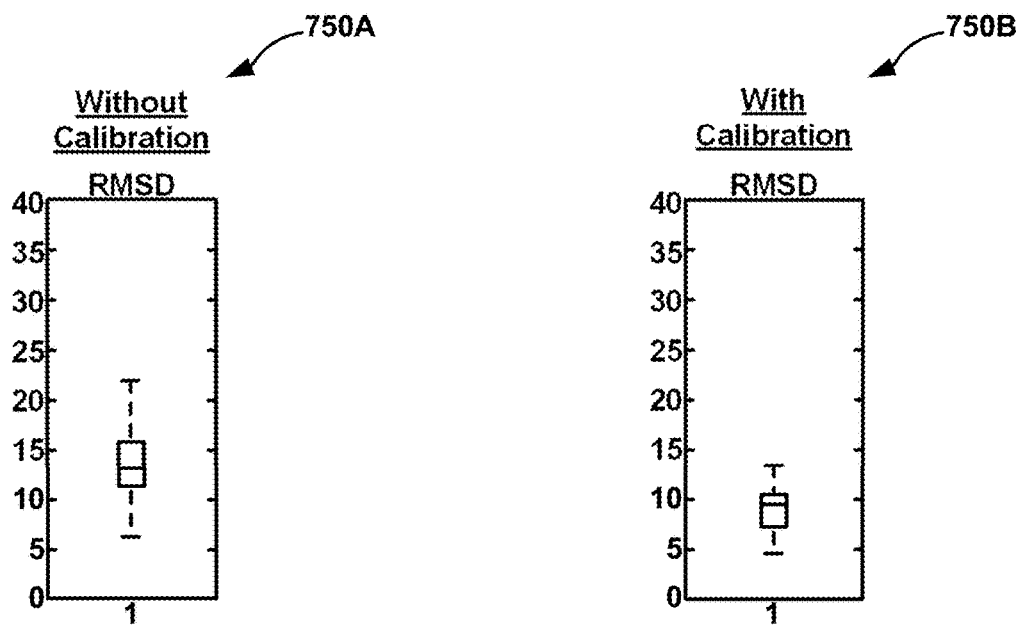

FIGS. 7A and 7B illustrate example graphs 700A, 700B, 750A, and 750B that depict the improvements in accuracy by determining the blood pressure of a patient using the CNIBP model 124 disclosed herein. As shown in FIG. 7A, graph 700A depicts the blood pressure, such as the mean arterial pressure, the systolic blood pressure, the diastolic blood pressure, and the like, of a patient measured via a blood pressure sensing device, such as an arterial line, and the blood pressure of a patient determined based at least in part on the PPG signals of the patient via a CNIBP model that has not been trained using calibration data. Meanwhile, graph 700B depicts the blood pressure, such as the mean arterial pressure, the systolic blood pressure, the diastolic blood pressure, and the like, of a patient measured via a blood pressure sensing device, such as an arterial line, and the blood pressure of a patient determined based at least in part on the PPG signals of the patient via a CNIBP model 124 that has been trained using calibration data, according to the techniques disclosed herein, such as via use of the neural network illustrated by deep learning architecture 500 in FIG. 5.

In the example of FIGS. 7A and 7B, the CNIBP model 124 may be implemented using MATLAB. Further, the PPG signals of the patient may be acquired using a pulse oximeter, and the features for CNIBP model 124 may be derived from 15 pulses (i.e., cardiac cycles) of the patient. As can be seen, the blood pressure of a patient determined via a CNIBP model 124 that has been trained using calibration data, as shown in graph 700B, tracks much more closely with the blood pressure of a patient measured via a blood pressure sensing device than the blood pressure of a patient determined via a CNIBP model that has not been trained using calibration data, as shown in graph 700A.

As shown in FIG. 7B, graph 750A depicts the measure of the differences between the blood pressure of a group of patients determined via a CNIBP model that has not been trained using calibration data and the blood pressure of a patient measured via a blood pressure sensing device. Conversely, graph 750B depicts the measure of the differences between the blood pressure of the same group of patients determined via a CNIBP model 124 that has been trained using calibration data and the blood pressure of a patient measured via a blood pressure sensing device. The measure of the differences illustrated in graphs 750A and 750B may be determined such as through root-mean-square deviation (RMSD). As can be seen from graphs 750A and 750B, the blood pressure of a group of patients determined via a CNIBP model 124 that has been trained using calibration data has a much smaller difference from the blood pressure of the patient than the blood pressure of the same group of patients determined via a CNIBP model that has not been trained using calibration data.

Figure 8:
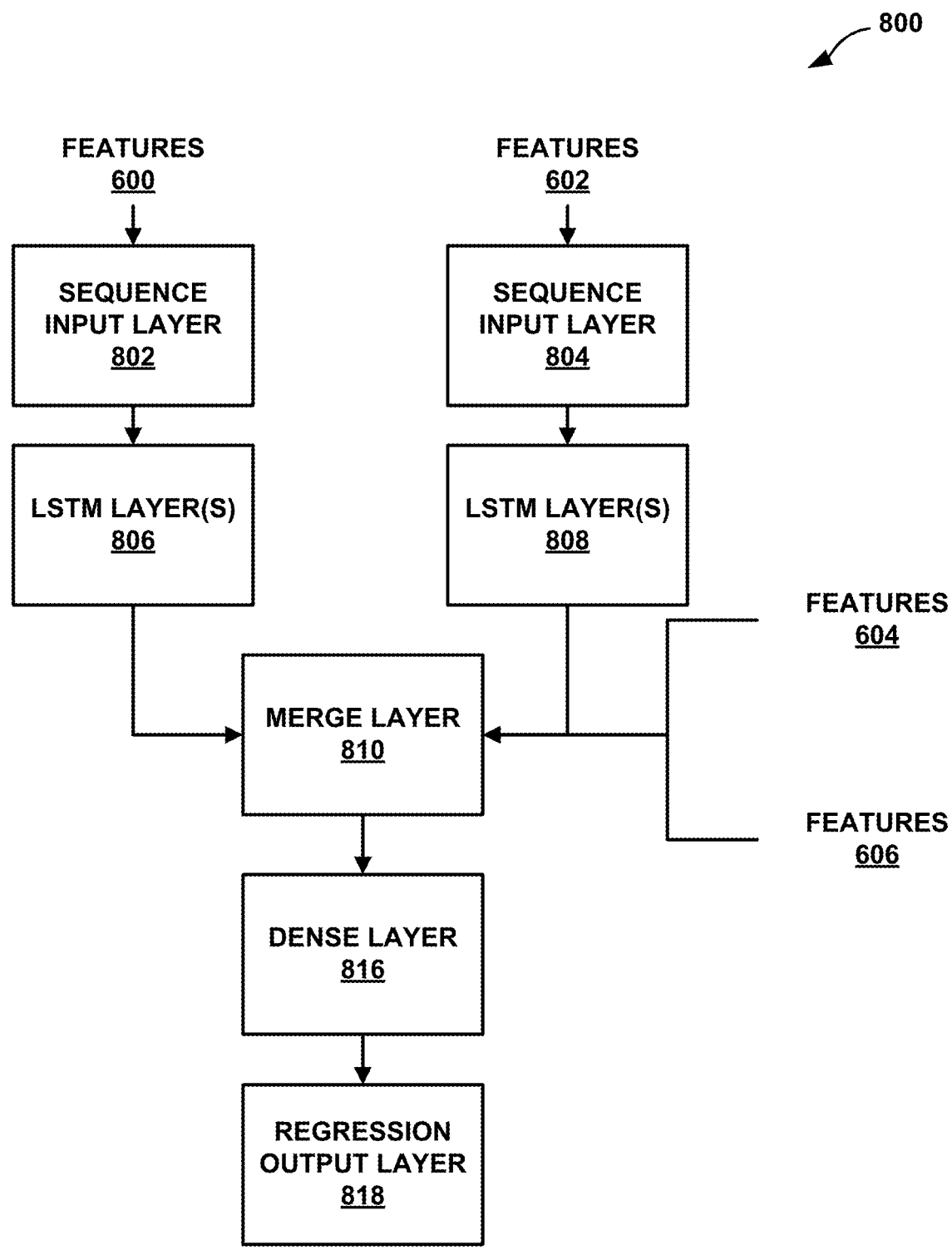
FIG. 8 illustrates an alternative example of a deep learning architecture of the CNIBP model of FIGS. 1 and 2.

FIG. 8 illustrates another example of a deep learning architecture 800 of CNIBP model 124 of FIGS. 1 and 2. Deep learning architecture 800 differs from deep learning architecture 500 shown in FIG. 5 in that features 604 and features 606 are separate inputs to the neural network of deep learning architecture 800 that are later combined within the network, such as through use of an addition or concatenation layer. This may enable the neural network to more easily learn relations between two feature sets, such as between features 600 determined at a particular time for determining a patient's blood pressure and features 602 determined at a most recent calibration point, compared with the neural network of deep learning architecture 500 where features 600, features 602, features 604, and features 606 are concatenated and inputted into deep learning architecture 500.

As shown in FIG. 8, deep learning architecture 800 includes sequence input layer 802, sequence input layer 804, one or more long short-term memory (LSTM) layers 806, one or more LSTM layers 808, merge layer 810, dense layer 816, and regression output layer 818. Sequence input layer 802 is connected to one or more LSTM layers 806. Sequence input layer 804 is connected to one or more LSTM layers 808. One or more LSTM layers 806 and one or more LSTM layers 808 are connected to merge layer 810. Merge layer 810 is connected to dense layer 816. Dense layer 816 is connected to regression output layer 818.

A sequence input layer such as sequence input layer 802 and sequence input layer 804 inputs sequence data to a neural network. Thus, sequence input layers 802 and 804 receive features that are used to train deep learning architecture 800. In the example of FIG. 8, sequence input layer 802 receives features 600 containing values of a set of metrics for a patient derived from a PPG signal received at the current time while sequence input layer 804 receives features 602 containing values of the same set of metrics for the patient derived from a PPG signal received at a most recent calibration point.

A LSTM layer, such as in one or more LSTM layers 806 and in one or more LSTM layers 808, learns long-term dependencies between time steps in a time series and sequence data. A LSTM layer performs additive interactions, which may help improve gradient flow over long sequences during training. In the example of FIG. 8, one or more LSTM layers 806 may receive input from sequence input layer 802, and one or more LSTM layers 808 may receive input from sequence input layer 804.

A merge layer, such as merge layer 810, may also be known as an addition layer or a concatenation layer. A merge layer adds inputs from multiple neural network layers element-wise. In the example of FIG. 8, merge layer 810 may add inputs from one or more LSTM layers 806, one or more LSTM layers 808, features 604, and features 606. Features 604 may be the elapsed time at the current time since the time of the most recent calibration point. Features 606 may be the blood pressure of the patient measured at the most recent calibration point.

A dense layer, such as dense layer 816, is a regular layer of neurons in a neural network. Each neuron in the layer of neurons may receive input from all the neurons in the previous layer. In the example of FIG. 8, each neuron in dense layer 816 may receive input from all the neurons in merge layer 810.

A regression output layer such as regression output layer 818 computes the half-mean-squared-error loss for regression problems and outputs a predicted response of the trained regression network as a result of training deep learning architecture 800. In the example of FIG. 8, regression output layer 818 receives the output of dense layer 816 and computes the half-mean-squared-error loss for regression problems to output a predicted blood pressure for the patient at the current time.

In some examples, instead of training CNIBP model 124 to predict the blood pressure of patient 101 at the current time, training system 200 may train CNIBP model 124 to predict a difference ($BP_{change}$) between the blood pressure of patient 101 measured at the most recent calibration point ($BP_{calib}$) and the blood pressure of patient 101 at the current time. Processing circuitry 110 can then determine the blood pressure of patient 101 at the current time by at least adding the blood pressure of the patient measured at the most recent calibration point and the difference between the blood pressure of the patient measured at the most recent calibration point and the blood pressure of the patient at the current time ($BP_{calib}+BP_{change}$).

FIG. 9 is a flow diagram illustrating an example method of determining the blood pressure of a patient using a CNIBP model 124. Although FIG. 9 is described with respect to processing circuitry 110 of CNIBP monitoring device 100 (FIG. 1), in other examples, different processing circuitry, alone or in combination with processing circuitry 110, may perform any part of the technique of FIG. 9. The technique illustrated in FIG. 9 includes determining, by processing circuitry 110, calibration data for a continuous non-invasive blood pressure model 124 at a calibration point by at least: receiving, by processing circuitry 110 from a blood pressure sensing device 152, a blood pressure signal (indicative of blood pressure of patient 101) at the calibration point, receiving, by processing circuitry 110 from an oxygen saturation sensing device 150, a first PPG signal (indicative of blood oxygen saturation of patient 101) at the calibration point, and deriving, by processing circuitry, first values of a set of metrics for the patient 101 from the first PPG signal (902). In some examples, the calibration point may encompass a specified time period, such as a single cardiac cycle.

In some examples, the continuous non-invasive blood pressure model 124 is a neural network algorithm trained via machine learning over training data that includes at least sets of calibration data at most recent calibration points of patient 101 (patient-specific data), and/or a population of patients, sets of elapsed time since the most recent calibration points, sets of PPG signals of patient 101 and/or the population of patients, and sets of target blood pressure values of patient 101 and/or the population of patients.

In some examples, the set of metrics for patient 101 comprises one or more of: a PPG pulse duration, a PPG relative position of a maximum upslope of a systolic rise, a PPG peak location and amplitude, a PPG perfusion index, a PPG baseline trend, a PPG respiratory cycle information, a PPG upstroke area, a PPG downstroke area, a maximum gradient of a PPG upslope, or a PPG baseline value.

The technique illustrated in FIG. 9 also includes receiving, by processing circuitry 110 and from the oxygen saturation sensing device 150, a second PPG signal at a particular time subsequent to the calibration point (904). The technique illustrated in FIG. 9 also includes deriving, by processing circuitry 110, second values of the set of metrics for the patient 101 from the second PPG signal (906). In some examples, the first values of the set of metrics comprises a first plurality of sequences of values over time, and the second values of the set of metrics comprises a second plurality of sequences of values over time.

The technique illustrated in FIG. 9 also includes determining, by processing circuitry 110 using the continuous non-invasive blood pressure model 124 and based at least in part on inputting the calibration data determined at the calibration point, the second values of the set of metrics, and an elapsed time at the particular time since the calibration point into the continuous non-invasive blood pressure model, a blood pressure of the patient 101 at the particular time (908).

In some examples, the technique illustrated in FIG. 3 also includes periodically determining, by processing circuitry 110, the calibration data for the continuous non-invasive blood pressure model 124 at a plurality of calibration points by at least: periodically receiving, by processing circuitry 110 from the blood pressure sensing device 152, the blood pressure measurement for the patient 101, periodically receiving, by processing circuitry from the oxygen saturation sensing device 150, a PPG signal for the patient 101, and periodically deriving, by processing circuitry 110, values of the set of metrics for the patient from the PPG signal, where the blood pressure measurement of the patient 101 at the calibration point and the first values of the set of metrics for the patient 101 comprise the calibration data at a most recent calibration point to the particular time out of the plurality of calibration points.

In some examples, the technique illustrated in FIG. 9 also includes, where the blood pressure measurement comprises a first blood pressure measurement, the calibration point comprises a first calibration point out of the plurality of calibration points, the particular time comprises a first particular time, determining, by processing circuitry 110, the calibration data for the continuous non-invasive blood pressure model 124 at a second calibration point out of the plurality of calibration points by at least: receiving, by processing circuitry 110 from the blood pressure sensing device 152, a second blood pressure measurement of the patient 101 at the second calibration point, receiving, by processing circuitry 110 from the oxygen saturation sensing device 150, a third PPG signal at the second calibration point, and deriving, by processing circuitry 110, third values of the set of metrics for the patient 101 from the third PPG signal. The second calibration point may be at a later time than the first calibration point.

In some examples, the technique illustrated in FIG. 9 also includes receiving, by processing circuitry 110 from the oxygen saturation sensing device 150, a fourth PPG signal at a second particular time subsequent to the second calibration point, wherein the second calibration point is the most recent calibration point to the second particular time. In some examples, the technique illustrated in FIG. 9 also includes deriving, by processing circuitry 110, fourth values of the set of metrics for patient 101 from the fourth PPG signal In some examples, the technique illustrated in FIG. 9 also includes determining, by processing circuitry 110 using the continuous non-invasive blood pressure model 124 and based at least in part on inputting the calibration data determined at the second calibration point, the fourth values of the set of metrics, and the elapsed time at the second particular time since the second calibration point into the continuous non-invasive blood pressure model 124, the blood pressure of patient 101 at the second particular time.

The techniques described in this disclosure, including those attributed to device 100, processing circuitry 110, control circuitry 122, sensing circuitries 140, 142, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices. Processing circuitry, control circuitry, and sensing circuitry, as well as other processors and controllers described herein, may be implemented at least in part as, or include, one or more executable applications, application modules, libraries, classes, methods, objects, routines, subroutines, firmware, and/or embedded code, for example.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. The computer-readable medium may be an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include RAM, ROM, programmable ROM (PROM), erasable programmable ROM (EPROM), electronically erasable programmable ROM (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

The functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements.

Example 1: In a first example, a method comprises determining calibration data for a continuous non-invasive blood pressure model at a calibration point, wherein determining the calibration data comprises: receiving a blood pressure measurement of a patient from a blood pressure sensing device at the calibration point, receiving a first photoplethysmographic (PPG) signal from an oxygen saturation sensing device at the calibration point, and deriving first values of a set of metrics for the patient from the first PPG signal. The method further comprises receiving a second PPG signal from the oxygen saturation sensing device at a particular time subsequent to the calibration point; deriving second values of the set of metrics for the patient from the second PPG signal; and determining, using the continuous non-invasive blood pressure model and based at least in part on inputting the calibration data determined at the calibration point, the second values of the set of metrics, and an elapsed time at the particular time since the calibration point into the continuous non-invasive blood pressure model, a blood pressure of the patient at the particular time.

Example 2: In some examples of Example 1, the continuous non-invasive blood pressure model comprises a neural network algorithm trained via machine learning over training data that includes at least sets of calibration data at most recent calibration points of a population of patients, sets of elapsed time since the most recent calibration points, sets of PPG signals of the population of patients, and sets of target blood pressure values of the population of patients.

Example 3: In some examples of Example 1 or Example 2, the continuous non-invasive blood pressure model comprises a neural network algorithm trained via machine learning over training data that includes at least sets of calibration data at calibration points of the patient, sets of elapsed time since the calibration points, sets of PPG signals of the patient, and sets of target blood pressure values of the patient Example 4: In some examples of any of Examples 1-3, the first values of the set of metrics comprises a first plurality of sequences of values over time; and the second values of the set of metrics comprises a second plurality of sequences of values over time.

Example 5: In some examples of Example 4, the set of metrics for the patient comprises one or more of: a PPG pulse duration, a PPG relative position of a maximum upslope of a systolic rise, a PPG peak location and amplitude, a PPG perfusion index, a PPG baseline trend, a PPG respiratory cycle information, a PPG upstroke area, a PPG downstroke area, a maximum gradient of a PPG upslope, or a PPG baseline value.

Example 6: In some examples of any of Examples 1-5, the method further comprises periodically determining the calibration data for the continuous non-invasive blood pressure model at a plurality of calibration points by at least: periodically receiving the blood pressure measurement for the patient from the blood pressure sensing device, periodically receiving a PPG signal from the oxygen saturation sensing device, and periodically deriving values of the set of metrics for the patient from the PPG signal, wherein the blood pressure measurement of the patient at the calibration point and the first values of the set of metrics for the patient comprise the calibration data at a most recent calibration point to the particular time out of the plurality of calibration points.

Example 7: In some examples of Example 6, the blood pressure measurement comprises a first blood pressure measurement, the calibration point comprises a first calibration point of the plurality of calibration points, and the particular time comprises a first particular time, the method further comprises: determining the calibration data for the continuous non-invasive blood pressure model at a second calibration point of the plurality of calibration points by at least: receiving a second blood pressure measurement of the patient from the blood pressure sensing device at the second calibration point, receiving a third PPG signal from the oxygen saturation sensing device at the second calibration point, and deriving third values of the set of metrics for the patient from the third PPG signal; receiving a fourth PPG signal from the oxygen saturation sensing device at a second particular time subsequent to the second calibration point, wherein the second calibration point is the most recent calibration point to the second particular time; deriving fourth values of the set of metrics for the patient from the fourth PPG signal; and determining, using the continuous non-invasive blood pressure model and based at least in part on inputting the calibration data determined at the second calibration point, the fourth values of the set of metrics, and the elapsed time at the second particular time since the second calibration point into the continuous non-invasive blood pressure model, the blood pressure of the patient at the second particular time.

Example 8: In some examples of any of Examples 1-7, determining the blood pressure of the patient at the particular time further comprises: determining, using the continuous non-invasive blood pressure model and based at least in part on the blood pressure measurements of the patient at the calibration point, the first values of the set of metrics, the second values of the set of metrics, and the elapsed time at the particular time since the calibration point, a predicted change in blood pressure between the calibration point and the particular time; and determining the blood pressure of the patient at the particular time based at least in part on the blood pressure measurement of the patient at the calibration point and the predicted change in blood pressure between the calibration point and the particular time.

Example 9: In some examples of any of Examples 1-8, the calibration point comprises a specified time period.

Example 10: In another example, a system comprises: a blood pressure sensing device; an oxygen saturation sensing device; and processing circuitry configured to: determine calibration data for a continuous non-invasive blood pressure model at a calibration point by at least: receiving, from the blood pressure sensing device, blood pressure measurements of a patient at the calibration point, receiving, from the oxygen saturation sensing device, a first photoplethysmographic (PPG) signal at the calibration point, and deriving first values of a set of metrics for the patient from the first PPG signal; receive, from the oxygen saturation sensing device, a second PPG signal at a particular time subsequent to the calibration point; derive second values of the set of metrics for the patient from the second PPG signal; and determine, using the continuous non-invasive blood pressure model and based at least in part on inputting the calibration data determined at the calibration point, the second values of the set of metrics, and an elapsed time at the particular time since the calibration point into the continuous non-invasive blood pressure model, a blood pressure of the patient at the particular time.

Example 11: In some examples of Example 10, the continuous non-invasive blood pressure model is a neural network algorithm trained via machine learning over training data that includes at least sets of calibration data at most recent calibration points of a population of patients, sets of elapsed time since the most recent calibration points, sets of PPG signals of the population of patients, and sets of target blood pressure values of the population of patients.

Example 12: In some examples of Example 10 or Example 11, the continuous non-invasive blood pressure model comprises a neural network algorithm trained via machine learning over training data that includes at least sets of calibration data at calibration points of the patient, sets of elapsed time since the calibration points, sets of PPG signals of the patient, and sets of target blood pressure values of the patient.

Example 13: In some examples of any of Examples 10-12, the first values of the set of metrics comprises a first plurality of sequences of values over time; and the second values of the set of metrics comprises a second plurality of sequences of values over time.

Example 14: In some examples of any of Examples 10-13, the set of metrics for the patient comprises one or more of: a PPG pulse duration, a PPG relative position of a maximum upslope of a systolic rise, a PPG peak location and amplitude, a PPG perfusion index, a PPG baseline trend, a PPG respiratory cycle information, a PPG upstroke area, a PPG downstroke area, a maximum gradient of a PPG upslope, or a PPG baseline value.

Example 15: In some examples of any of Examples 10-15, the processing circuitry is further configured to: periodically determine the calibration data for the continuous non-invasive blood pressure model at a plurality of calibration points by at least: periodically receiving, from the blood pressure sensing device, the blood pressure measurement for the patient, periodically receiving, from the oxygen saturation sensing device, a PPG signal for the patient, and periodically deriving values of the set of metrics for the patient from the PPG signal; and wherein the blood pressure measurement of the patient at the calibration point and the first values of the set of metrics for the patient comprise the calibration data at a most recent calibration point to the particular time out of the plurality of calibration points.

Example 16: In some examples of Example 15, the blood pressure measurement comprises a first blood pressure measurement, the calibration point comprises a first calibration point out of the plurality of calibration points, the particular time comprises a first particular time, and the processing circuitry is further configured to: determine the calibration data for the continuous non-invasive blood pressure model at a second calibration point out of the plurality of calibration points by at least: receiving, from the blood pressure sensing device, a second blood pressure measurement of the patient at the second calibration point, receiving, from the oxygen saturation sensing device, a third PPG signal at the second calibration point, and deriving third values of the set of metrics for the patient from the third PPG signal; receive, from the oxygen saturation sensing device, a fourth PPG signal at a second particular time subsequent to the second calibration point, wherein the second calibration point is the most recent calibration point to the second particular time; derive fourth values of the set of metrics for the patient from the fourth PPG signal; and determine, using the continuous non-invasive blood pressure model and based at least in part on inputting the calibration data determined at the second calibration point, the fourth values of the set of metrics, and the elapsed time at the second particular time since the second calibration point into the continuous non-invasive blood pressure model, the blood pressure of the patient at the second particular time.

Example 17: In some examples of any of Examples 10-16, the processing circuitry that is configured to determine the blood pressure of the patient at the particular time is further configured to: determine, using the continuous non-invasive blood pressure model and based at least in part on the blood pressure measurements of the patient at the calibration point, the first values of the set of metrics, the second values of the set of metrics, and the elapsed time at the particular time since the calibration point, a predicted change in blood pressure between the calibration point and the particular time; and determine the blood pressure of the patient at the particular time based at least in part on the blood pressure measurement of the patient at the calibration point and the predicted change in blood pressure between the calibration point and the particular time.

Example 18: In some examples of any of Examples 10-17, the calibration point comprises a specified time period.

Example 19: In another example, a non-transitory computer readable storable medium comprising instructions that, when executed, cause processing circuitry to: determine calibration data for a continuous non-invasive blood pressure model at a calibration point by at least: receiving blood pressure measurements of a patient at the calibration point, receiving a first photoplythysmographic (PPG) signal at the calibration point, and deriving first values of a set of metrics for the patient from the first PPG signal; receive a second PPG signal at a particular time subsequent to the calibration point; derive second values of the set of metrics for the patient from the second PPG signal; and determine, using the continuous non-invasive blood pressure model and based at least in part on inputting the calibration data determined at the calibration point, the second values of the set of metrics, and an elapsed time at the particular time since the calibration point into the continuous non-invasive blood pressure model, a blood pressure of the patient at the particular time.

Example 20: In some examples of Example 19, the continuous non-invasive blood pressure model is a neural network algorithm trained via machine learning over training data that includes at least sets of calibration data at most recent calibration points of a population of patients, sets of elapsed time since the most recent calibration points, sets of PPG signals of the population of patients, and sets of target blood pressure values of the population of patients.

Various examples of the disclosure have been described. Any combination of the described systems, operations, or functions is contemplated. These and other examples are within the scope of the following claims.

What is claimed is:

1. A method comprising:
    determining calibration data for a continuous non-invasive blood pressure model at a calibration point, wherein determining the calibration data comprises:
        receiving a blood pressure measurement of a patient from a blood pressure sensing device at the calibration point,
        receiving a first photoplethysmographic (PPG) signal from an oxygen saturation sensing device at the calibration point, and
        deriving first values of a set of metrics for the patient from the first PPG signal;
    receiving a second PPG signal from the oxygen saturation sensing device at a particular time subsequent to the calibration point;
    deriving second values of the set of metrics for the patient from the second PPG signal; and
    determining, using the continuous non-invasive blood pressure model and based at least in part on inputting the calibration data determined at the calibration point, the second values of the set of metrics, and an elapsed time at the particular time since the calibration point into the continuous non-invasive blood pressure model, a blood pressure of the patient at the particular time.

2. The method of claim 1, wherein the continuous non-invasive blood pressure model comprises a neural network algorithm trained via machine learning over training data that includes at least sets of calibration data at most recent calibration points of a population of patients, sets of elapsed time since the most recent calibration points, sets of PPG signals of the population of patients, and sets of target blood pressure values of the population of patients.

3. The method of claim 1, wherein the continuous non-invasive blood pressure model comprises a neural network algorithm trained via machine learning over training data that includes at least sets of calibration data at calibration points of the patient, sets of elapsed time since the calibration points, sets of PPG signals of the patient, and sets of target blood pressure values of the patient.

4. The method of claim 1, wherein:
the first values of the set of metrics comprises a first plurality of sequences of values over time; and
the second values of the set of metrics comprises a second plurality of sequences of values over time.

5. The method of claim 4, wherein the set of metrics for the patient comprises one or more of: a PPG pulse duration, a PPG relative position of a maximum upslope of a systolic rise, a PPG peak location and amplitude, a PPG perfusion index, a PPG baseline trend, a PPG respiratory cycle information, a PPG upstroke area, a PPG downstroke area, a maximum gradient of a PPG upslope, or a PPG baseline value.

6. The method of claim 1, further comprising:
periodically determining the calibration data for the continuous non-invasive blood pressure model at a plurality of calibration points by at least:
periodically receiving the blood pressure measurement for the patient from the blood pressure sensing device,
periodically receiving a PPG signal from the oxygen saturation sensing device, and
periodically deriving values of the set of metrics for the patient from the PPG signal,
wherein the blood pressure measurement of the patient at the calibration point and the first values of the set of metrics for the patient comprise the calibration data at a most recent calibration point to the particular time out of the plurality of calibration points.

7. The method of claim 6, wherein the blood pressure measurement comprises a first blood pressure measurement, the calibration point comprises a first calibration point of the plurality of calibration points, and the particular time comprises a first particular time, the method further comprising:
determining the calibration data for the continuous non-invasive blood pressure model at a second calibration point of the plurality of calibration points by at least:
receiving a second blood pressure measurement of the patient from the blood pressure sensing device at the second calibration point,
receiving a third PPG signal from the oxygen saturation sensing device at the second calibration point, and
deriving third values of the set of metrics for the patient from the third PPG signal;
receiving a fourth PPG signal from the oxygen saturation sensing device at a second particular time subsequent to the second calibration point, wherein the second calibration point is the most recent calibration point to the second particular time;
deriving fourth values of the set of metrics for the patient from the fourth PPG signal; and
determining, using the continuous non-invasive blood pressure model and based at least in part on inputting the calibration data determined at the second calibration point, the fourth values of the set of metrics, and the elapsed time at the second particular time since the second calibration point into the continuous non-invasive blood pressure model, the blood pressure of the patient at the second particular time.

8. The method of claim 1, wherein determining the blood pressure of the patient at the particular time further comprises:
determining, using the continuous non-invasive blood pressure model and based at least in part on the blood pressure measurements of the patient at the calibration point, the first values of the set of metrics, the second values of the set of metrics, and the elapsed time at the particular time since the calibration point, a predicted change in blood pressure between the calibration point and the particular time; and
determining the blood pressure of the patient at the particular time based at least in part on the blood pressure measurement of the patient at the calibration point and the predicted change in blood pressure between the calibration point and the particular time.

9. The method of claim 1, wherein the calibration point comprises a specified time period.

10. A system comprising:
a blood pressure sensing device;
an oxygen saturation sensing device; and
processing circuitry configured to:
determine calibration data for a continuous non-invasive blood pressure model at a calibration point by at least:
receiving, from the blood pressure sensing device, blood pressure measurements of a patient at the calibration point,
receiving, from the oxygen saturation sensing device, a first photoplethysmographic (PPG) signal at the calibration point, and
deriving first values of a set of metrics for the patient from the first PPG signal;
receive, from the oxygen saturation sensing device, a second PPG signal at a particular time subsequent to the calibration point;
derive second values of the set of metrics for the patient from the second PPG signal; and
determine, using the continuous non-invasive blood pressure model and based at least in part on inputting the calibration data determined at the calibration point, the second values of the set of metrics, and an elapsed time at the particular time since the calibration point into the continuous non-invasive blood pressure model, a blood pressure of the patient at the particular time.

11. The system of claim 10, wherein the continuous non-invasive blood pressure model is a neural network algorithm trained via machine learning over training data that includes at least sets of calibration data at most recent calibration points of a population of patients, sets of elapsed time since the most recent calibration points, sets of PPG signals of the population of patients, and sets of target blood pressure values of the population of patients.

12. The system of claim 10, wherein the continuous non-invasive blood pressure model comprises a neural network algorithm trained via machine learning over training data that includes at least sets of calibration data at calibration points of the patient, sets of elapsed time since the calibration points, sets of PPG signals of the patient, and sets of target blood pressure values of the patient.

13. The system of claim 10, wherein:
the first values of the set of metrics comprises a first plurality of sequences of values over time; and
the second values of the set of metrics comprises a second plurality of sequences of values over time.

14. The system of claim 10, wherein the set of metrics for the patient comprises one or more of: a PPG pulse duration, a PPG relative position of a maximum upslope of a systolic rise, a PPG peak location and amplitude, a PPG perfusion index, a PPG baseline trend, a PPG respiratory cycle information, a PPG upstroke area, a PPG downstroke area, a maximum gradient of a PPG upslope, or a PPG baseline value.

15. The system of claim 10, wherein the processing circuitry is further configured to:
- periodically determine the calibration data for the continuous non-invasive blood pressure model at a plurality of calibration points by at least:
  - periodically receiving, from the blood pressure sensing device, the blood pressure measurement for the patient,
  - periodically receiving, from the oxygen saturation sensing device, a PPG signal for the patient, and
  - periodically deriving values of the set of metrics for the patient from the PPG signal; and
- wherein the blood pressure measurement of the patient at the calibration point and the first values of the set of metrics for the patient comprise the calibration data at a most recent calibration point to the particular time out of the plurality of calibration points.

16. The system of claim 15, wherein the blood pressure measurement comprises a first blood pressure measurement, the calibration point comprises a first calibration point out of the plurality of calibration points, the particular time comprises a first particular time, and the processing circuitry is further configured to:
- determine the calibration data for the continuous non-invasive blood pressure model at a second calibration point out of the plurality of calibration points by at least:
  - receiving, from the blood pressure sensing device, a second blood pressure measurement of the patient at the second calibration point,
  - receiving, from the oxygen saturation sensing device, a third PPG signal at the second calibration point, and
  - deriving third values of the set of metrics for the patient from the third PPG signal;
- receive, from the oxygen saturation sensing device, a fourth PPG signal at a second particular time subsequent to the second calibration point, wherein the second calibration point is the most recent calibration point to the second particular time;
- derive fourth values of the set of metrics for the patient from the fourth PPG signal; and
- determine, using the continuous non-invasive blood pressure model and based at least in part on inputting the calibration data determined at the second calibration point, the fourth values of the set of metrics, and the elapsed time at the second particular time since the second calibration point into the continuous non-invasive blood pressure model, the blood pressure of the patient at the second particular time.

17. The system of claim 10, wherein the processing circuitry that is configured to determine the blood pressure of the patient at the particular time is further configured to:
- determine, using the continuous non-invasive blood pressure model and based at least in part on the blood pressure measurements of the patient at the calibration point, the first values of the set of metrics, the second values of the set of metrics, and the elapsed time at the particular time since the calibration point, a predicted change in blood pressure between the calibration point and the particular time; and
- determine the blood pressure of the patient at the particular time based at least in part on the blood pressure measurement of the patient at the calibration point and the predicted change in blood pressure between the calibration point and the particular time.

18. The system of claim 10, wherein the calibration point comprises a specified time period.

19. A non-transitory computer readable storable medium comprising instructions that, when executed, cause processing circuitry to:
- determine calibration data for a continuous non-invasive blood pressure model at a calibration point by at least:
  - receiving blood pressure measurements of a patient at the calibration point,
  - receiving a first photoplethysmographic (PPG) signal at the calibration point, and
  - deriving first values of a set of metrics for the patient from the first PPG signal;
- receive a second PPG signal at a particular time subsequent to the calibration point;
- derive second values of the set of metrics for the patient from the second PPG signal; and
- determine, using the continuous non-invasive blood pressure model and based at least in part on inputting the calibration data determined at the calibration point, the second values of the set of metrics, and an elapsed time at the particular time since the calibration point into the continuous non-invasive blood pressure model, a blood pressure of the patient at the particular time.

20. The computer readable storable medium of claim 19, wherein the continuous non-invasive blood pressure model is a neural network algorithm trained via machine learning over training data that includes at least sets of calibration data at most recent calibration points of a population of patients, sets of elapsed time since the most recent calibration points, sets of PPG signals of the population of patients, and sets of target blood pressure values of the population of patients.

* * * * *